US012642667B2

(12) United States Patent
Troxell et al.

(10) Patent No.: US 12,642,667 B2
(45) Date of Patent: Jun. 2, 2026

(54) INTERBODY FUSION SYSTEM

(71) Applicant: GLOBUS MEDICAL, INC., Audubon, PA (US)

(72) Inventors: Paden Troxell, Conshohocken, PA (US); David C. Paul, Phoenixville, PA (US); Norbert Johnson, North Andover, MA (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 18/882,819

(22) Filed: Sep. 12, 2024

(65) Prior Publication Data

US 2026/0069424 A1 Mar. 12, 2026

Related U.S. Application Data

(63) Continuation of application No. 18/882,020, filed on Sep. 11, 2024.

(51) Int. Cl.
*A61F 2/44* (2006.01)
*A61F 2/46* (2006.01)

(52) U.S. Cl.
CPC .... *A61F 2/4455* (2013.01); *A61F 2002/4615* (2013.01)

(58) Field of Classification Search
CPC .......... A61F 2/44; A61F 2/442; A61F 2/4425; A61F 2/4455; A61F 2002/443; A61F 2002/444; A61F 2002/4445; A61F 2002/445; A61F 2002/3067; A61B 5/4851; A61B 5/686; A61B 17/7002; A61B 2560/0468

USPC ............................................. 623/17.11–17.16
See application file for complete search history.

(56) References Cited

U.S. PATENT DOCUMENTS

| | | | |
|---|---|---|---|
| 7,179,295 B2 * | 2/2007 | Kovacevic | A61F 2/4657 623/20.32 |
| 2002/0049394 A1 * | 4/2002 | Roy | A61B 5/4504 623/17.11 |
| 2005/0113932 A1 * | 5/2005 | Kovacevic | A61F 2/4657 606/280 |
| 2005/0273170 A1 * | 12/2005 | Navarro | A61F 2/442 600/595 |
| 2017/0007420 A1 * | 1/2017 | Stevenson | A61B 5/076 |

(Continued)

*Primary Examiner* — Jacqueline T Johanas
*Assistant Examiner* — Christina Negrellirodriguez

(57) ABSTRACT

An interbody spacer configured for implantation between spinal vertebrae. The interbody spacer including electrical circuitry within an electronics housing of the interbody spacer and a plurality of load sensors spaced apart on carriers of the interbody spacer. The plurality of load sensors electrically connectable to the electrical circuitry and configured to provide to the electrical circuitry a load signal indicative of a measurement of force exerted onto the plurality of load sensors of the interbody spacer. The interbody spacer further including a plurality of electrodes spaced apart on a surface of the interbody spacer. The plurality of electrodes electrically connectable to the electrical circuitry and configured to at least one of provide to the electrical circuitry an electrode signal indicative of an impedance measurement and generate an electrical field between at least two electrodes of the plurality of electrodes.

11 Claims, 25 Drawing Sheets

(56)                    References Cited

U.S. PATENT DOCUMENTS

| 2022/0305258 A1 * | 9/2022 | Zellmer | ................ | A61F 2/4455 |
| 2023/0110885 A1 * | 4/2023 | Molnar | ................ | A61N 1/0551 |
| | | | | 607/46 |

* cited by examiner

TETHER CONNECTOR & DRIVE FEATURE FOR ATTACHMENT SCREW

ELECTRONICS MODULE

EXTERNAL SENSING & STIMULATION ELECTRODES

INTERNAL SENSING & STIMULATION ELECTRODES

220

FLEXIBLE CARRIERS

LINEAR STRAIN GAUGES

502a

Platinum Conductor Traces

Polyimide Dielectric Core

Polyimide Coverlay

Polyimide Coverlay

Polyimide Dielectric Core

Platinum Conductor Traces

Electroplated Platinum

Electroplated Silver-chloride

Electroplated Silver

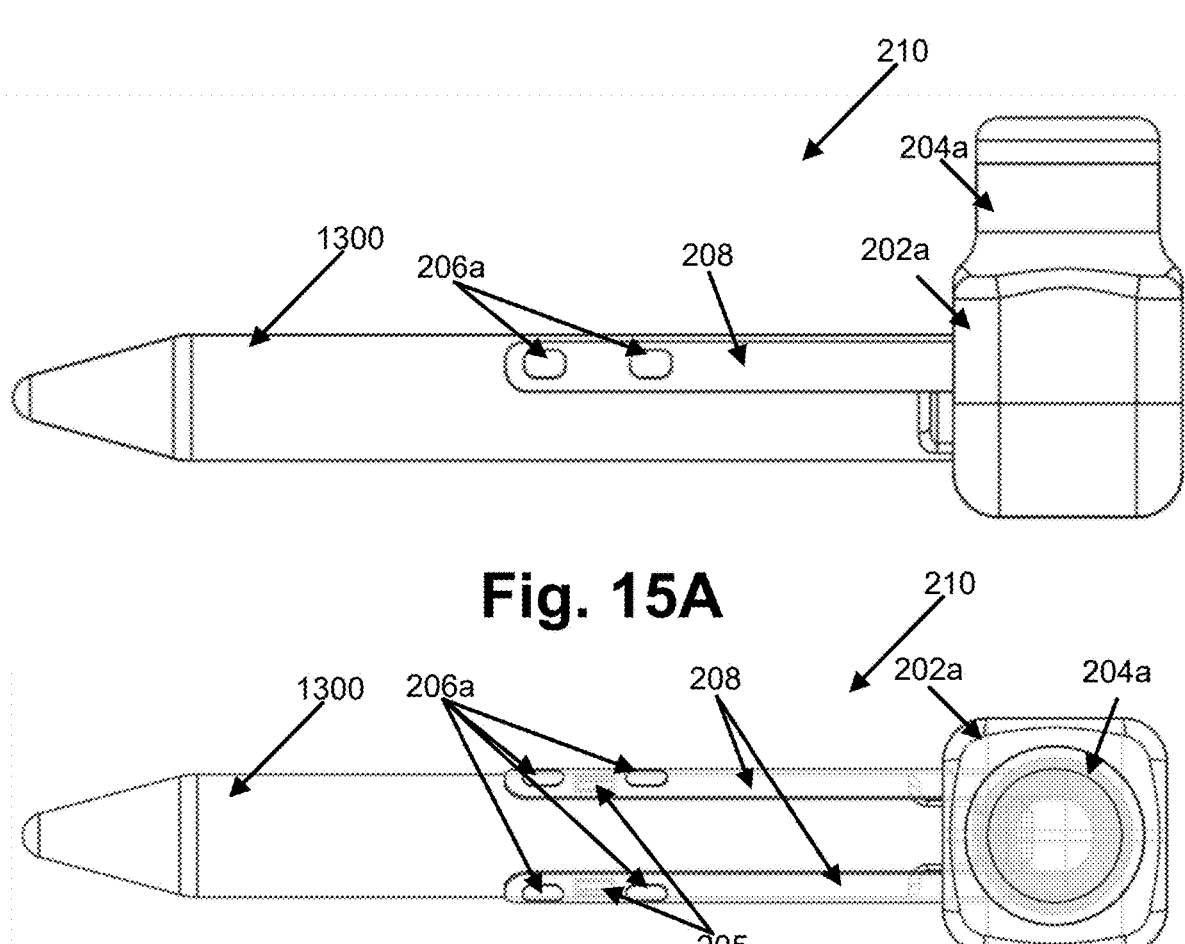
Fig. 15A
Fig. 15B
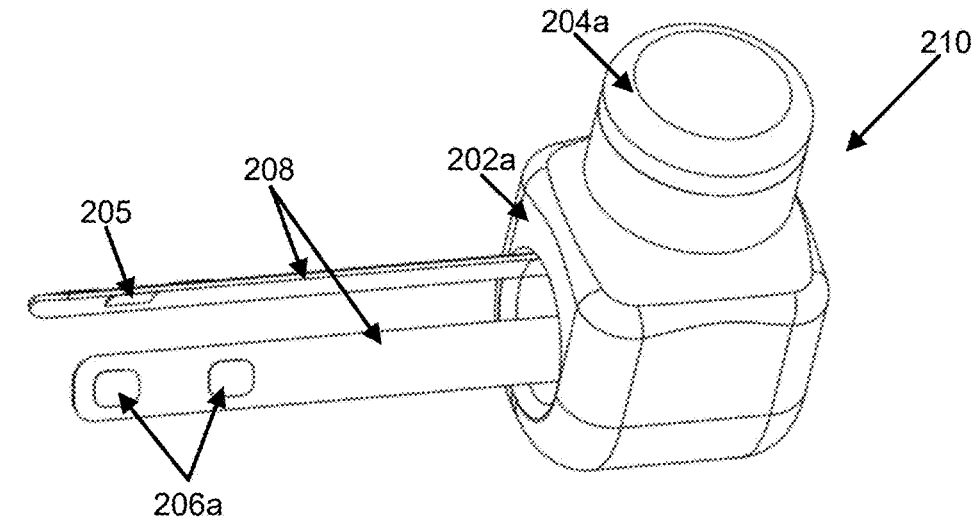
Fig. 15C

1600

1602

1602

Electronics Module & Rechargeable Battery 1702

Wireless Power & Data Transceivers 1704

1602

Wearable Device

INTERBODY FUSION SYSTEM

CROSS REFERENCE TO RELATED APPLICATIONS

This application is a continuation application of U.S. patent application Ser. No. 18/882,020 filed on Sep. 11, 2024, which is incorporated in its entirety herein.

FIELD

The present disclosure relates to medical implants, including musculoskeletal implants.

BACKGROUND

Lumbar spine fusion involves the use of interbody spacers and posterior fixation implants (e.g., pedicle screws, rods, locking caps) to decompress neural elements, restore anatomic alignment, and provide structural support to the spinal column while bone grows and heals between affected vertebral bodies. Despite advances in implant technologies and surgical techniques, outcomes of lumbar spine fusion remain inconsistent and insufficient.

One primary failure mode of lumbar interbody fusion is pseudarthrosis, which is the lack of formation of a contiguous boney bridge between adjacent vertebral bodies. Causes of pseudarthrosis include but are not limited to insufficient stabilization of the construct, low osteogenic activity (e.g., history of smoking), and the formation of infection-causing biofilm on implant surfaces. Pseudarthrosis often results in cyclic loosening at the bone-implant interfaces, degradation of the boney interfaces, and fatigue-related breakage of implant components. These failures have cascading consequences to the musculoskeletal system, including fracture, pain, and numbness, and often requires more invasive revision surgery.

Another common failure mode occurs when the interbody spacer subsides into the adjacent endplate as fusion occurs, resulting in a loss of corrected disc height and anatomic alignment. In this scenario, the vertebrae successfully fuse, however, the patient often experiences persistent pain and numbness at the operative levels due to insufficient neural decompression. Subsidence is generally considered time-dependent phenomena akin to creep, where the bone deforms over time due an applied load that is less than the yield strength of the bone.

SUMMARY

Some embodiments of the present disclosure are directed an interbody spacer configured for implantation between spinal vertebrae. The interbody spacer including electrical circuitry within an electronics housing of the interbody spacer. The interbody spacer further including a plurality of load sensors spaced apart on carriers of the interbody spacer. The plurality of load sensors electrically connectable to the electrical circuitry and configured to receive power from the electrical circuitry and provide to the electrical circuitry a load signal indicative of a measurement of force exerted onto the plurality of load sensors of the interbody spacer. The interbody spacer further including a plurality of electrodes spaced apart on a surface of the interbody spacer. The plurality of electrodes being electrically connectable to the electrical circuitry and configured to receive power from the electrical circuitry. The plurality of electrode further configured to at least one of provide to the electrical circuitry an electrode signal indicative of an impedance measurement indicating impedance of biological material surrounding the plurality of electrodes or a presence of biofilm surrounding the plurality of electrodes and generate an electrical field between at least two electrodes of the plurality of electrodes to electrically stimulate biological materials adjacent the at least two electrodes to a level which reduces biofilm or promotes bone growth.

Some other embodiments of the present disclosure are directed to an implant rod configured for spinal interbody fusion. The implant rod including electrical circuitry within an electronics housing of the implant rod. The implant rod further including a plurality of load sensors spaced apart on carriers of the implant rod. The plurality of load sensors electrically connectable to the electrical circuitry and configured to receive power from the electrical circuitry and provide to the electrical circuitry a load signal indicative of a measurement of force exerted onto the plurality of load sensors of the implant rod. The implant rod further including a plurality of electrodes spaced apart on a surface of the implant rod. The plurality of electrodes electrically connectable to the electrical circuitry and configured to receive power from the electrical circuitry. The plurality of electrode further configured to at least one of provide to the electrical circuitry an electrode signal indicative of an impedance measurement indicating impedance of biological material surrounding the plurality of electrodes or a presence of biofilm surrounding the plurality of electrodes and generate an electrical field between the plurality of electrodes to electrically stimulate biological material adjacent the at least two electrodes to a level which reduces biofilm or promotes bone growth.

DESCRIPTION OF THE DRAWINGS

Aspects of the present disclosure are illustrated by way of example and are not limited by the accompanying drawings. In the drawings:

FIGS. 15A-C illustrates the smart rod fully assembled in FIGS. 15A-B and removed from the rod in FIG. 15C, according to some embodiments of the present disclosure;

DETAILED DESCRIPTION

Figure 1:
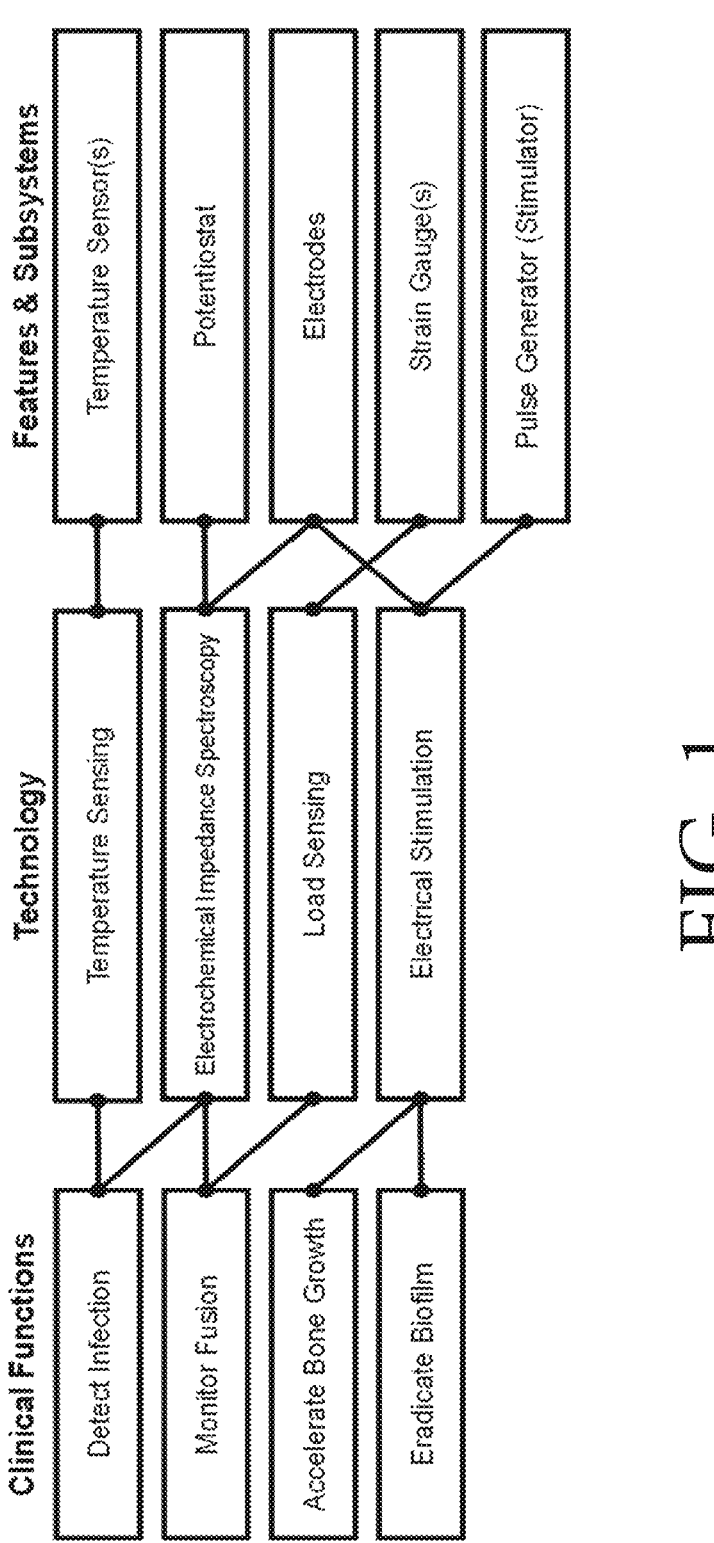
FIG. 1 illustrates clinical functions, technology, and features/subsystems of the interbody fusion system, according to some embodiments of the present disclosure.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

With respect to both failure modes, there is a physiologic race between the formation of new bone and mechanical failure of the native bone or implant components. Embodiments of the present disclosure helps solve at least these issues by increasing the rate of bone formation, decreasing the rate of implant/bone failure, or a combination of both.

Some embodiments of the present disclosure are directed to spinal implants that have electronic circuits ("smart implants") which operate to provide physicians and/or their patients the operational ability to treat, monitor, detect, and diagnose infection and to detect and promote bone growth. The present disclosure discusses a smart interbody fusion system that address both clinical objectives by augmenting lumbar interbody fusion implants with sensing and treatment systems. The implants of the present disclosure may provide a cost-effective way of integrating electronics within traditional mechanical implant form factors.

FIG. 1 illustrates clinical functions, technology, and features/subsystems of the interbody fusion system, according to some embodiments of the present disclosure. Some primary clinical functions of the proposed smart interbody fusion system may include one or more of: to detect infection, monitor fusion, accelerate bone growth, and eradicate biofilm. Some of these primary functions may be accomplished by a one or more of temperature sensing, electrochemical impedance spectroscopy (EIS), load sensing, and electrical stimulation.

Infection detection may be enabled by a combination of measuring local, in situ temperature changes as a biomarker of the body's inflammatory response to infection as well as direct measurement of the presence of implant biofilm, which is the precursor to deep surgical site infection (SSI). The smart implants described herein may include one or more integrated digital temperature sensor integrated circuits (ICs). In isolation, temperature data may not be a specific or reliable indicator of SSI. For example, in the acute and post-acute period (day 0-14) some amount of inflammation and local elevated temperature rise may be expected due to the body's response to the surgery, including the healing process. However, after initial healing occurs and the body returns to a new baseline, any subsequent local temperature elevations may indicate the early stages of infection. These local temperature elevations could serve as important early warning signals of infection before the infection fully develops and causes a systemic response (e.g. fever).

An additional or alternative way the smart implants my detect infection is through an impedance measurement that indicates the presence of infection-causing biofilm on the surfaces of the implant components. Biofilm sensing is enabled by electrochemical impedance spectroscopy (EIS) techniques. To facilitate EIS, the smart implants may include electrodes on one or more surfaces of the implant components, which act as the electrochemical cell, as well as a potentiostat IC or subsystem, which sends signals (e.g., at a range of frequencies from 1 Hz to 1 MHz) to the electrochemical cell (within the electrical circuitry, discussed in further details below) and interprets the signal response. The potentiostat IC or subsystem may be included in the electrical circuitry described herein that is housed within the electronics housing. The electrical circuitry may further include processors, battery and/or capacitive circuitry, power transfer circuitry (for directing power to the different components of the implant and through a tether discussed below), memory, etc. that enables the functionality discussed herein.

From this signal response, a model (i.e. digital twin) of the electrochemical environment on and around the surface of the electrode can be constructed. This model is referred to as an equivalent circuit of the electrochemical system. From this model, the presence of a biofilm layer developed on the surface of the electrode can be determined, as the biofilm represents a circuit element within the equivalent circuit model. In addition, the value of this circuit element (e.g. 4 kΩ) can be correlated with physical properties of the biofilm, such as the thickness or cell density, as a measure of the biofilm maturity. Often, infection only occurs after a biofilm is mature and well-established, which takes 24-72 hours in an in vitro setting but 14-28 days in an in vivo environment. By monitoring biofilm growth of biofilm over time, the system may provide clinicians up to 28 days of early warning before any infection symptoms occur, including local temperature elevations and systemic responses such as fever.

By combining both biofilm-sensing (via impedance measurements) and temperature sensing functions, the proposed smart implant system may provide clinicians an unparalleled tool for clinical decision making, including follow-up protocols and treatment plans. In addition, the data collected by this system could be used to train diagnostic algorithms that are sufficiently accurate and reliable to provide clinical diagnosis of infection. In the long term, these biofilm and infection diagnostic algorithms could be coupled with a biofilm eradication system (discussed in detail below) to form a closed-loop infection prevention and treatment system which requires no intervention from the clinician or patient.

Fusion monitoring may be enabled by a combination of measuring changes in strain of the implant components as well as measuring changes in impedance of the tissue surrounding the implants over time. Strain measurements may be accomplished with one or more strain gauges integrated within or adhered to the surfaces of load-bearing implant components (e.g., carriers of the implant). In addition, the strain sensing system may include one or more precision resistors to complete a Wheatstone bridge circuit that is coupled with an analog-to-digital converter (ADC) and microcontroller (MCU) (within the electrical circuitry of the implant) to amplify and read the changes in signal. A robust model of the loading conditions (e.g. resultant force vector magnitude and location) on the implant can be assessed from strain gauges positioned in multiple locations and orientations on the implant surfaces. This model of the in situ loading conditions can then be used to monitor the changes in loading conditions over time. As a boney bridge forms between adjacent vertebrae during the fusion process, the new bone will share dynamic loads with the implant construct. This load sharing results in a decreasing trend of strain on the implant components, which can be measured with the strain sensing system. Collectively, this data may provide surgeons an estimation of fusion progress as a function of implant loading. Additionally, the strain sensing system may also be used to monitor for acute changes in loading conditions as a marker of mechanical failure and may also serve as an important data collection platform to advance clinical and biomechanics research.

An additional or alternative way of monitoring fusion progress involves measurement of the changes in impedance of the adjacent tissues over time. The impedance measurement system leverages the same set of electrodes and potentiostat subsystem (included in the electrical circuitry of the implant) that was previously described. Each distinct type of tissue has unique dielectric properties which can be measured and correlated with EIS techniques. By measuring the impedance of the adjacent graft material over time, the system may enable the clinician to assess the change in tissue type from aggregate graft material to cortical bone. Additionally, the impedance values can also be correlated with bone mineral density measurements to not only report the formation of bone, but more specifically the bone mineral density of that bone tissue. With the addition of electrical impedance tomography (EIT) post-processing algorithms, this system may also construct a 3D visualization of the tissue location and composition surrounding the implant.

By combining both strain sensing and tissue impedance sensing functions, the proposed smart implant system may provide clinicians a robust tool for clinical decision making, including healing assessments, follow-up protocols, and treatment plans. In addition, the data collected by this system could be used to train diagnostic algorithms that are sufficiently accurate and reliable to provide clinical diagnosis of delayed fusion, non-fusion, and mechanical breakage. In the long term, these diagnostic algorithms could be coupled with the bone growth stimulation system described later in this disclosure to form a closed-loop fusion enhancement system which automatically steers the stimulation and adjusts the dosage without intervention from the clinician or patient.

Bone growth acceleration may be enabled by electrical stimulation, which exploits the natural bone modeling process and enhances osteogenic activity. Cathodic-biased current pulses are delivered to the adjacent bone graft tissues using the same or a different set of electrodes that were previously described in this disclosure. The current-controlled pulses are generated by a pulse generator within an electronics module, which may include the previously described potentiostat IC or a dedicated circuit. The stimulation current may be biased cathodic because cathodic current is more effective at inducing osteogenic activity, such as ALP expression, as compared to anodic current. Biphasic pulses are employed to balance charges between the designated anode and cathode electrodes. In addition, the maximum voltage is set to 1.5V or less to avoid electrolysis, and the pulse frequency ranges between 0.5 Hz and 100 Hz with a pulse duration of <1 millisecond and amplitude less than 1 mA. The system and accompanying software will enable the clinician to program the stimulation treatment. Programming will enable the clinician to set which electrodes are activated along with the treatment current amplitude, frequency, pulse profile, pulse duration, and total treatment duration.

For example, the electrical circuitry of the interbody spacer (or the smart rod) may generate the electrical field between the plurality of electrodes as cathodic-biased current pulses.

One example of a program would consist of a biphasic square-wave with a frequency of 10 Hz, pulse duration of 0.5 milliseconds, and amplitude of 100 µA. This program can then be prescribed within a treatment protocol, which could consist of 1 hour of treatment per week for 24 weeks. Over time, the clinician-specified treatment programs can be correlated with measured fusion outcomes to assess which programs and protocols are most effective for a particular patient population.

These treatment parameters may also be specified in infection treatment instructions from the clinician (discussed below).

Electrical stimulation is also an effective treatment against infection-causing biofilm. One method of electrical stimulation may include a brief pulse of low current (i.e. microamperes) that is sufficient to compromise the cellular wall of adhered bacterial cells without causing acute toxicity or histologic damage to the nearby tissues. The biofilm treatment system may include the electrodes that make up an electrode array and electrical stimulation system previously described in this disclosure. In addition, metallic implant components may also be electrically coupled with the stimulation system to serve as electrodes. For example, a conductive screw, conductive housing, and/or conductive locking cap may be electrically stimulated to treat infection or promote bone growth. An electric field may be formed between the metallic implant component and an electrode of the implant that is physically connected to the metallic implant component. In this configuration, biofilm could be eradicated from all conductive implant components, including the screws and locking caps, which may not directly possess any electrical components but are electrically connected to the electronics module.

For example, an electrical circuitry of the smart rod may be electrically coupled to at least one of a conductive locking cap that is physically attached to the implant rod and a conductive pedicle screw that is attached to the locking cap. The electrical circuitry may be configured to generate an electrical field between the conductive locking cap and/or the pedicle screw and an electrode of the plurality of electrodes to a level which reduces biofilm.

In another example, an electrical circuitry of an interbody spacer may be electrically coupled to a conductive screw that is physically attached to the interbody spacer, wherein the electrical circuitry of the interbody spacer is configured to generate an electrical field between the conductive screw and an electrode of the plurality of electrodes.

A biased biphasic pulsed current similar to what is used for electrical stimulation may also be employed for biofilm treatment. A difference between the biofilm treatment and the bone growth treatment may include that the biofilm treatment duration is shorter in duration, for example 1 second, and the current amplitude might be higher, for example 1 mA.

The metallic implant components may be electrically stimulated by either the electrical circuitry within the interbody spacer or the smart rod. In some embodiments, the implant that electrically stimulates the metallic implant is based on which implant the metallic implant component is physically connected to. However, in some embodiments, a metallic implant component may be electrically stimulated by a physically separate implant through a tether that electrically connects the physically separate implant to the metallic implant component.

Below, further details of a physical embodiment of the smart interbody fusion system is discussed with reference to minimally invasive transforaminal lumbar interbody fusion (MIS TLIF), however, the disclosed concepts apply to all interbody fusion approaches and implants.

Figure 2:
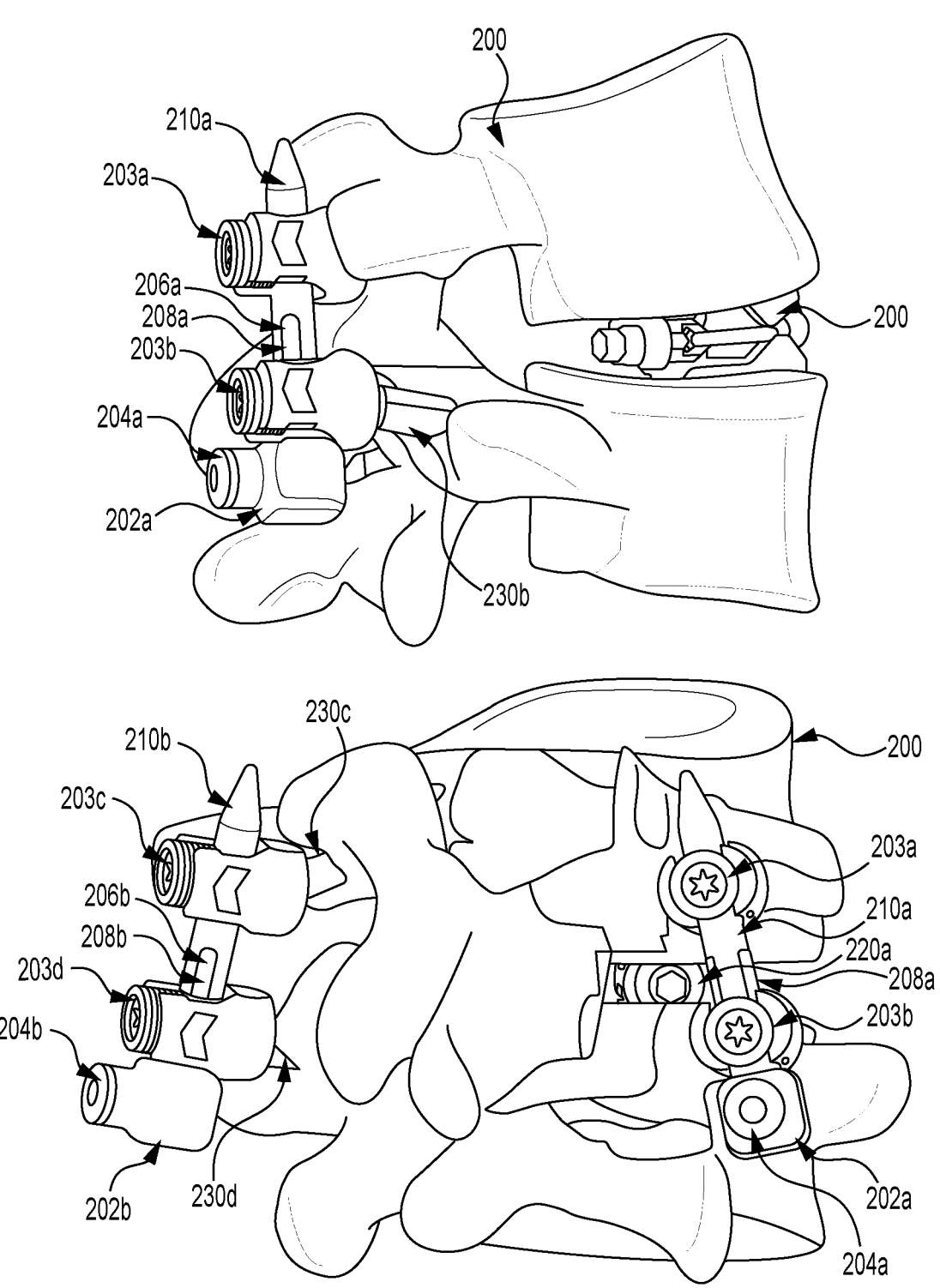
FIG. 2 illustrates a smart interbody fusion system including a smart interbody spacer and smart rods implanted into a spine of a patient, according to some embodiments of the present disclosure.

FIG. 2 illustrates a smart interbody fusion system including a smart interbody spacer 220 and smart rods 210*a-b* implanted into a spine 200 of a patient, according to some embodiments of the present disclosure.

Figure 3A:
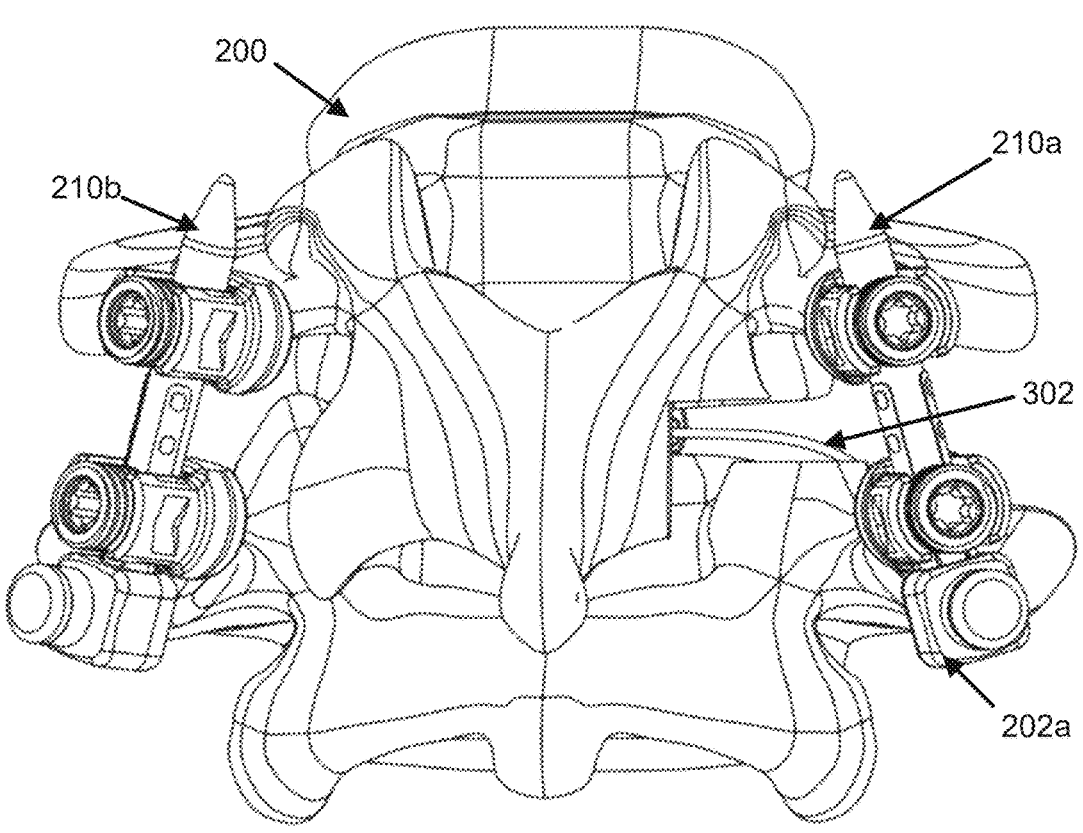
FIGS. 3A-B illustrate the smart interbody fusion system including a tether between the smart interbody spacer and one of the smart rods, according to some embodiments of the present disclosure.
Figure 3B:
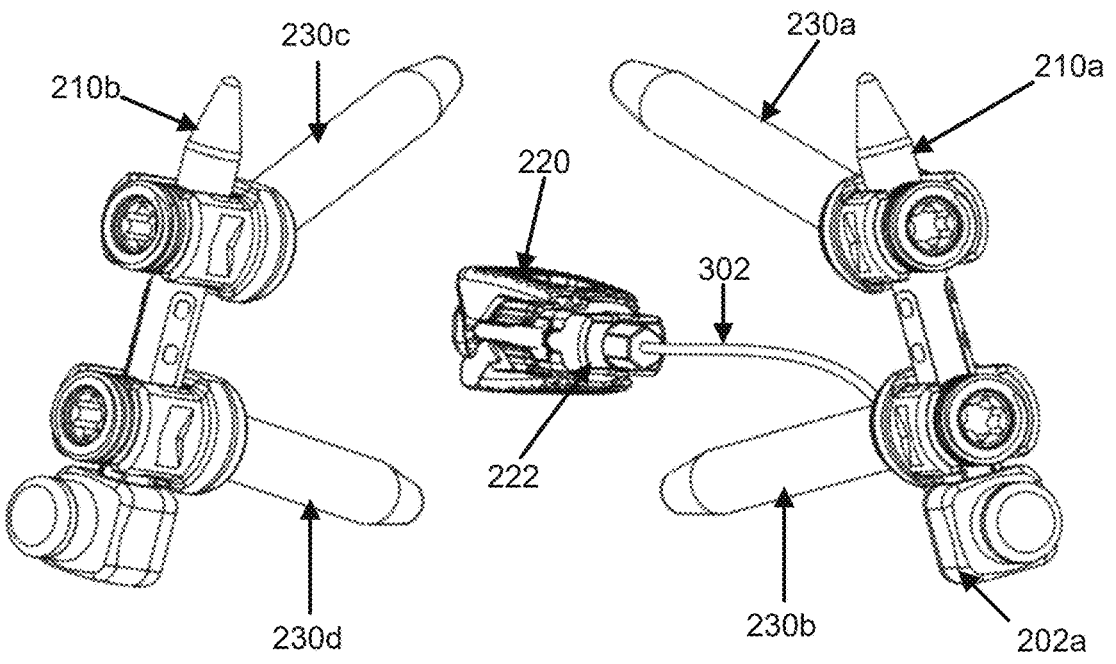
Figure 4A:
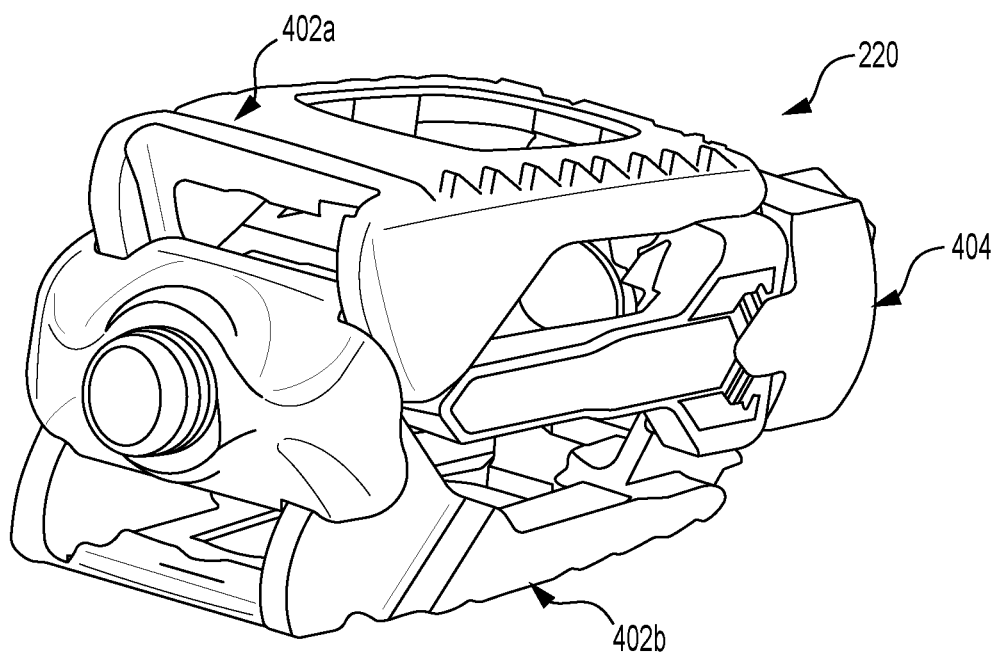
FIGS. 4A-D illustrate different viewing angles of the smart interbody spacer, according to some embodiments of the present disclosure.
Figure 4B:
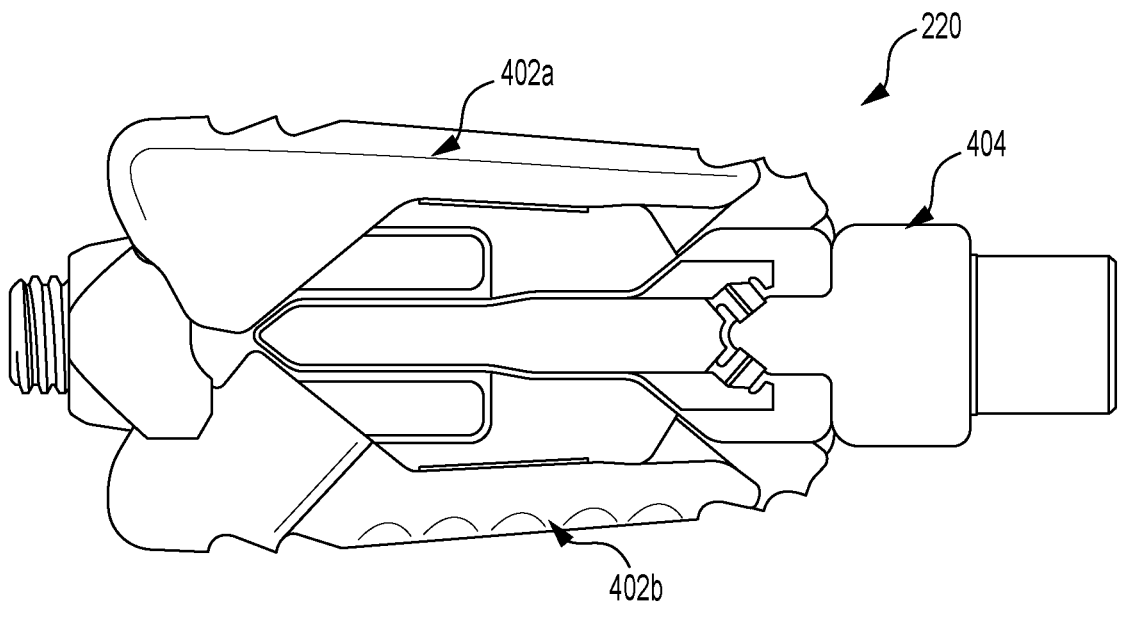
Figure 4C:
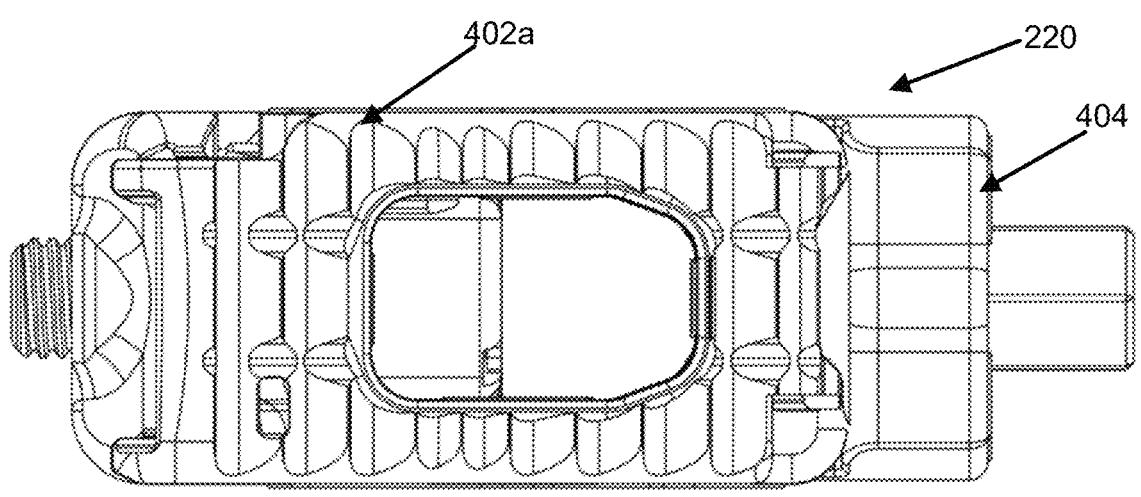
Figure 4D:
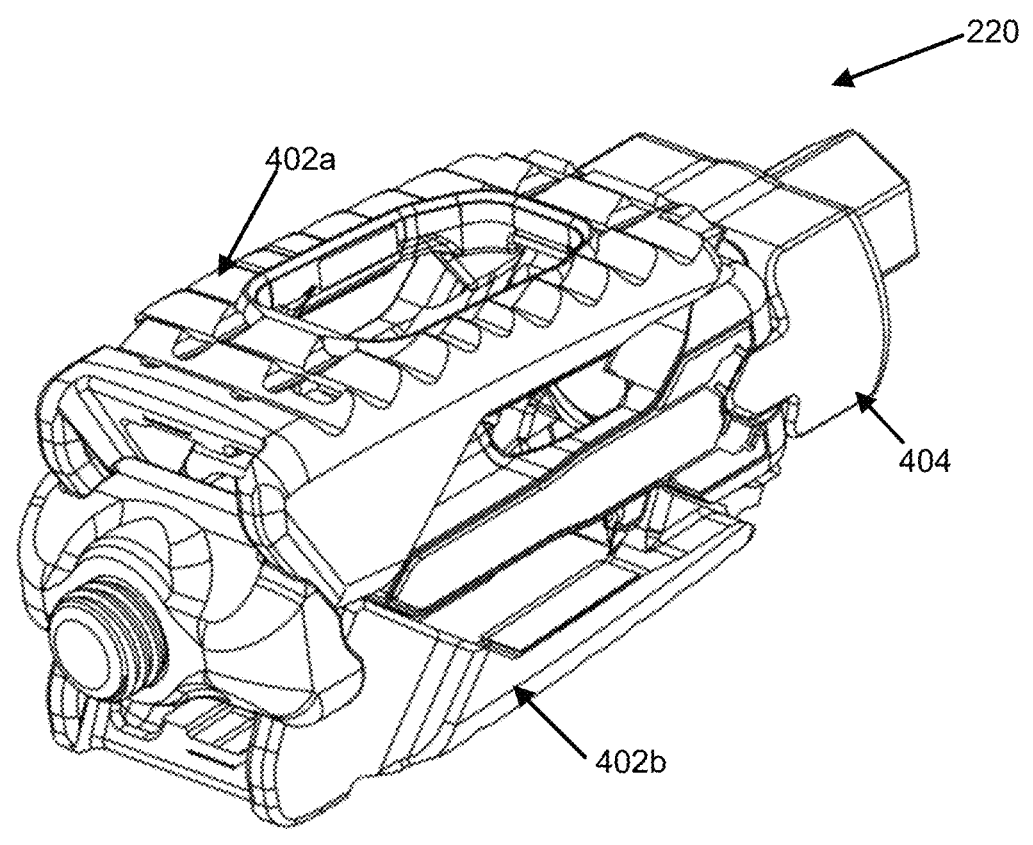

FIGS. 3A-B illustrate the smart interbody fusion system including a tether 302 between the smart interbody spacer 220 and one of the smart rods (smart rod 210*a*), according to some embodiments of the present disclosure.

With reference to both FIG. 2 and FIGS. 3A-B, the smart rods may be configured for spinal interbody fusion. The smart rods 210*a-b* may include electrical circuitry within an electronics housing (collectively referred herein as an electronics module 202*a-b*). The electronics modules 202*a-b* are connected to one or more carriers 208*a-b* that include electrodes 206*a-b* on a surface of the carriers 208*a-b* and are electrically connected to the electrical circuitry within the electronics module 202*a-b*, respectively.

In some embodiments, the smart rod (e.g., smart rod 210 of FIG. 13) includes a plurality of electrodes spaced apart on a surface of the implant rod. The plurality of electrodes may be electrically connectable to the electrical circuitry and configured to receive power from the electrical circuitry. The plurality of electrodes may also be configured to at least one of: (1) provide to the electrical circuitry an electrode signal indicative of an impedance measurement indicating impedance of biological materials surrounding the plurality of electrodes or a presence of biofilm surrounding the plurality of electrodes, and (2) generate an electrical field between the plurality of electrodes to electrically stimulate biological materials adjacent the at least two electrodes to a level which reduces biofilm or promotes bone growth.

The biological materials may include tissue, fluid, and/or bone of a patient.

In some embodiments, the smart rod (e.g., smart rod 210 of FIGS. 15A-C) includes a plurality of load sensors (e.g., strain gauges) spaced apart on the carriers of the implant rod. The plurality of load sensors may be electrically connectable to the electrical circuitry and configured to receive power from the electrical circuitry and provide to the electrical circuitry a load signal indicative of a measurement of force exerted onto the plurality of load sensors of the implant rod.

The carriers 208*a-b* may be attached to or integrated within a rod that extends out from the electronics modules 202*a-b*. The smart rods 210*a-b* may each be connected through the rod to pedicle screws (230*a-d*) through locking caps 203*a-d*, and the pedicle screw and locking caps may be electrically coupled to an electrical circuitry within an electronics module of the smart rod it is connected to. This electrical coupling may allow for the pedicle screws 230*a-d* and/or locking caps 203*a-d* to be stimulated to reduce biofilms or promote bone growth even though the pedicle screws 230*a-d* and locking caps 203*a-d* may not possess any integrated electronic components.

The pedicle screws 230*a-d* may be screwed into the spine above and below where the smart interbody spacer 220 is implanted between spinal vertebrae.

In some embodiments, the smart rods 210*a-b* include a wireless power and communication interface 204*a-b* that is electrically connected to the electrical circuitry of the respective smart rod. The wireless power and communication interface 204*a-b* is configured to wirelessly receive power and/or data from an external device (discussed below) while the smart rod is implanted within a body of the patient and the external device is located external to the body of the patient. The wireless power and communication interface 204*a-b* may be configured to transfer the received power and/or data through the tether to an electrical circuitry of the interbody spacer 220.

The electrical module 202*a* of the smart rod 210*a* may be connected to an electrical module 222 of the smart interbody spacer 220 through the tether 302. The tether is discussed in further detail below.

FIGS. 4A-D illustrate different viewing angles of the smart interbody spacer 220, according to some embodiments of the present disclosure.

The smart interbody spacer 220 includes an expandable posterior lumbar interbody spacer with porous 3D printed titanium endplates 402*a-b* and an integrated intelligent healing system that enables in situ bone growth stimulation, fusion monitoring, infection detection, and biofilm eradiation. The interbody may be inserted at a contracted height as low as 6 mm to reduce disruption during insertion and provides up to 8 mm of expansion and 22° of lordosis. The integrated intelligent healing system includes several subsystems including electrochemical sensing, electrical stimulation, strain sensing, temperature sensing, and motion sensing. The intelligent healing system includes an electronics module 404 and carriers.

For example, the smart interbody spacer 220 may include a temperature sensor. The temperature sensor may be configured to receive power from the electrical circuitry and to provide a temperature measurement signal to the electrical circuitry. In some embodiments, the temperature sensor is located within the electronics housing.

Figure 5A:
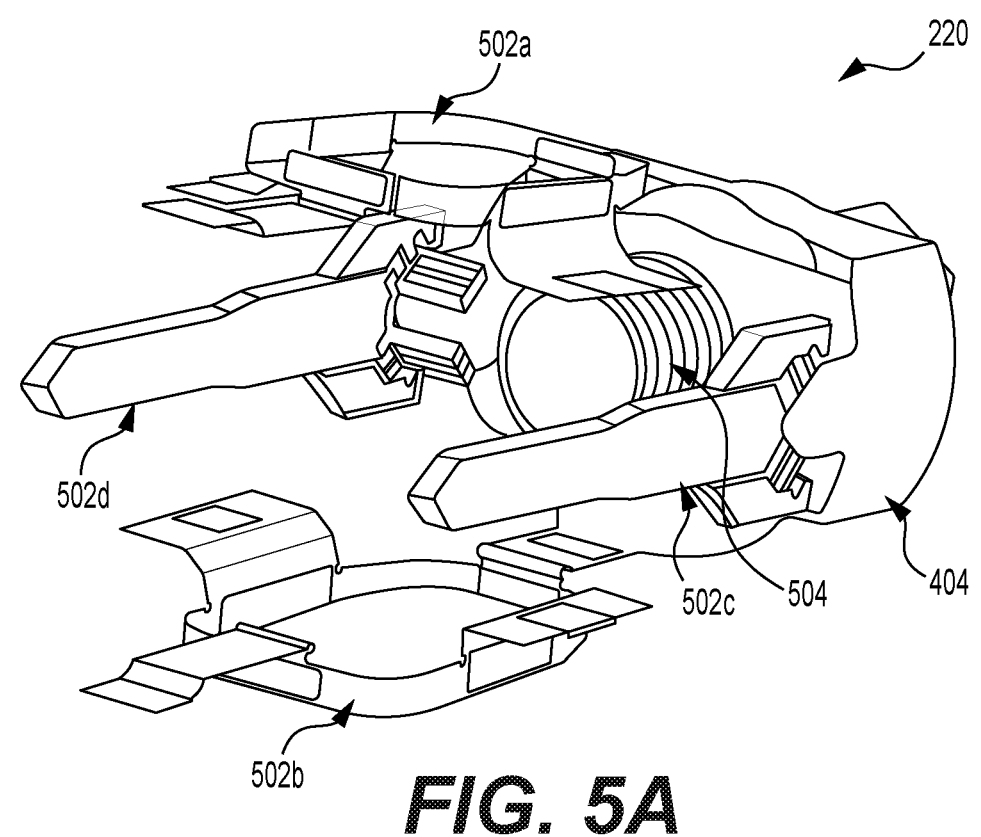
FIGS. 5A-C illustrate an electronics module and carriers that are integrated within the smart interbody spacer, according to some embodiments of the present disclosure.
Figure 5B:
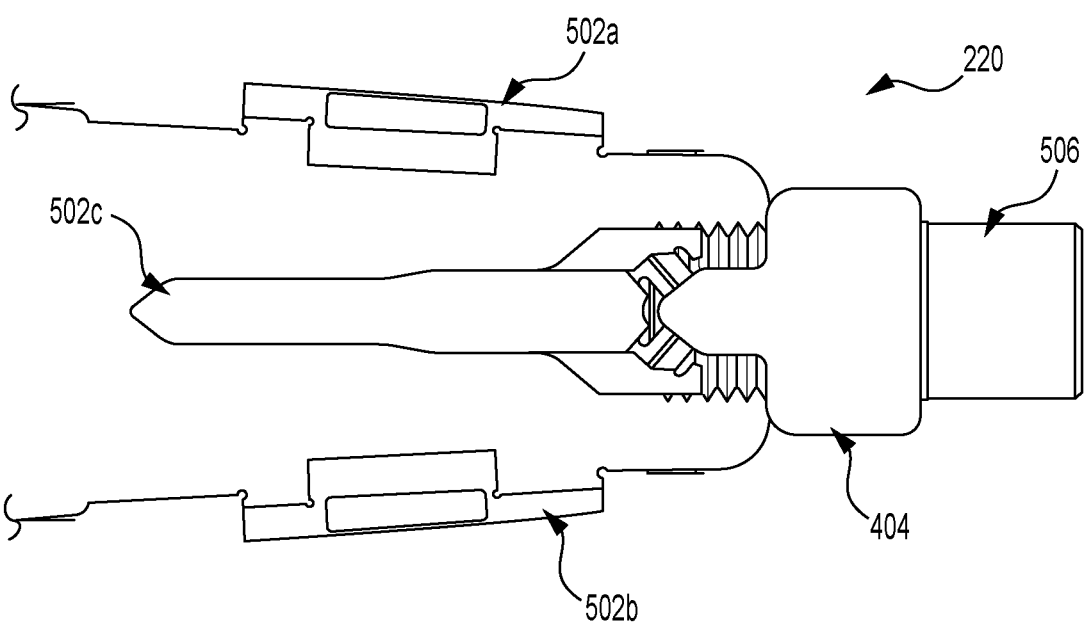
Figure 5C:
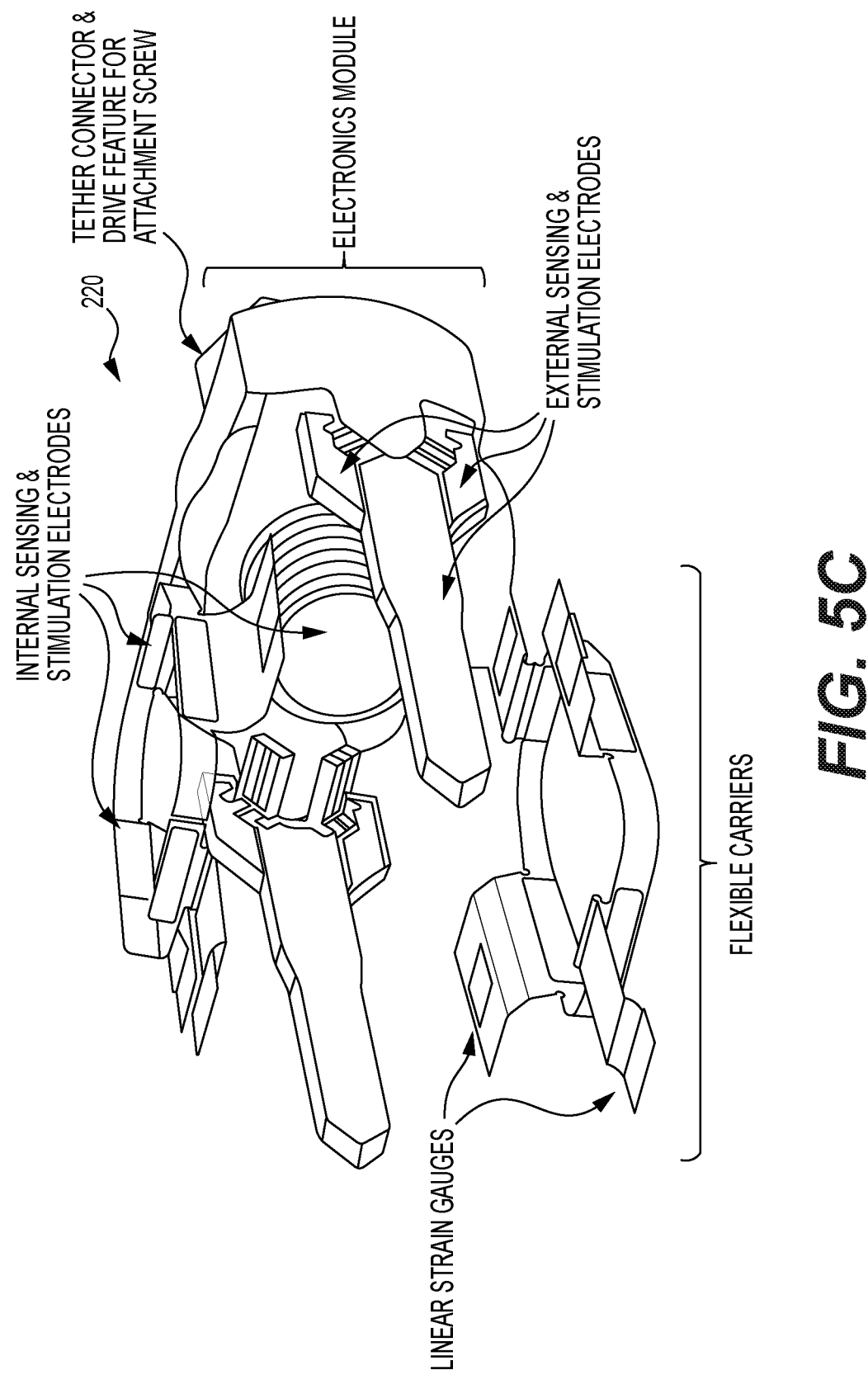

FIGS. 5A-C illustrate the electronics module 404 and carriers 502a-d that are integrated within the smart interbody spacer 220, according to some embodiments of the present disclosure.

In some embodiments, the interbody spacer 220 is configured for implantation between spinal vertebrae and includes electrical circuitry within an electronics housing of the interbody spacer. The interbody spacer 220 further includes a plurality of load sensors (e.g., load sensors shown in FIGS. 5C and 9B) spaced apart on carriers of the interbody spacer 220. The plurality of load sensors may be electrically connectable to the electrical circuitry and configured to receive power from the electrical circuitry. The plurality of load sensors may be further configured to provide to the electrical circuitry a load signal indicative of a measurement of force exerted onto the plurality of load sensors of the interbody spacer 220.

The interbody spacer 220 may further include a plurality of electrodes spaced apart on a surface of the interbody spacer, the plurality of electrodes (e.g., electrodes shown in FIGS. 5C and 9A) electrically connectable to the electrical circuitry and configured to receive power from the electrical circuitry. The plurality of electrodes may be further configured to at least one of: (1) provide to the electrical circuitry an electrode signal indicative of an impedance measurement indicating impedance of biological materials surrounding the plurality of electrodes or a presence of biofilm surrounding the plurality of electrodes, and (2) generate an electrical field between at least two electrodes of the plurality of electrodes to electrically stimulate biological materials adjacent the at least two electrodes to a level which reduces biofilm or promotes bone growth.

The electronics module 404 houses the electrical circuitry that may include one or more of a temperature sensor, inertial measurement unit (IMU), and other circuit elements that enable electrochemical sensing and electrical stimulation functions. The carriers 502a-d house the electrodes and strain gauges and distribute electrical signals between these elements and electronics module 404. The mechanical structure of the expandable interbody is hidden in FIGS. 5A-C to illustrate how the electronics module 404 and carriers are 502a-d integrated within the interbody structure.

The smart interbody spacer 220 further comprises a tether connector and drive feature 506 for an attachment screw 504 that removably attached the electronics module and carriers to the expandable interbody of the interbody spacer. This attachment screw 504 may include an electrode (e.g., at an end of the screw) that is configured to obtain measurements and perform electrical stimulation for reducing infection or promoting biofilm.

Additionally, or alternatively, the attachment screw 504 may include conductive material and may be electrically connected to the electronics module 404. In these embodiments, the attachment screw 504 may be configured to be electrically stimulated by the electrical circuitry in the electronics module 404 to a level that reduces infection or promotes biofilm.

Figure 6A:
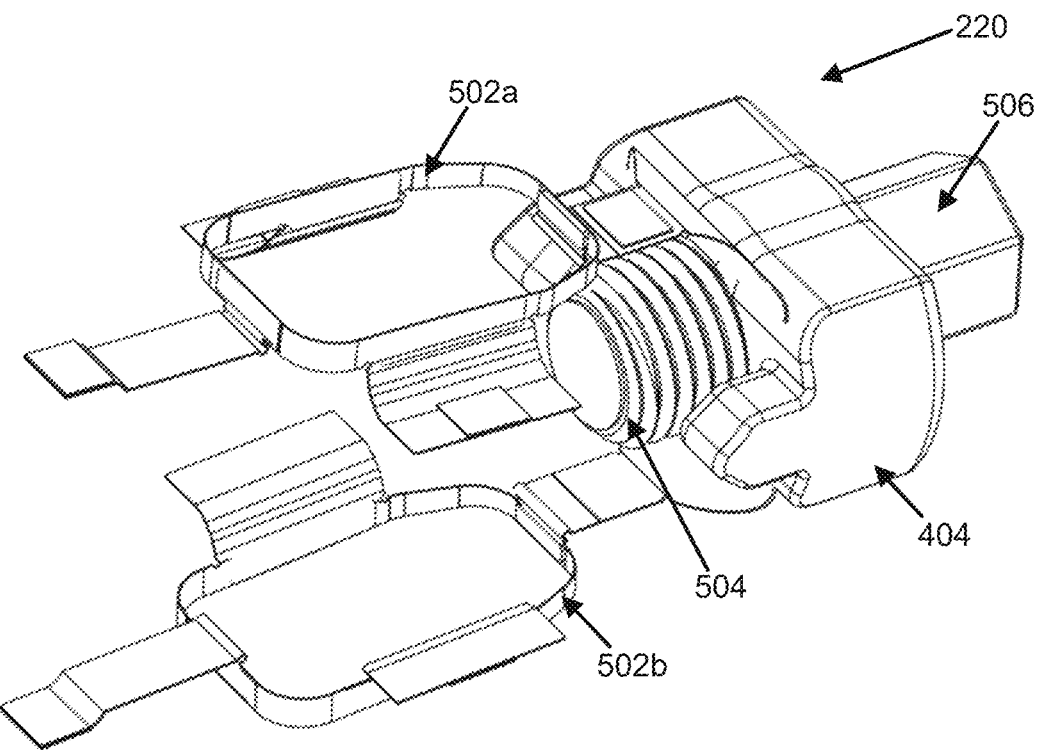
FIG. 6A-B illustrates the electronics module and two end plate carriers that are integrated within the smart interbody spacer, according to some embodiments of the present disclosure.
Figure 6B:
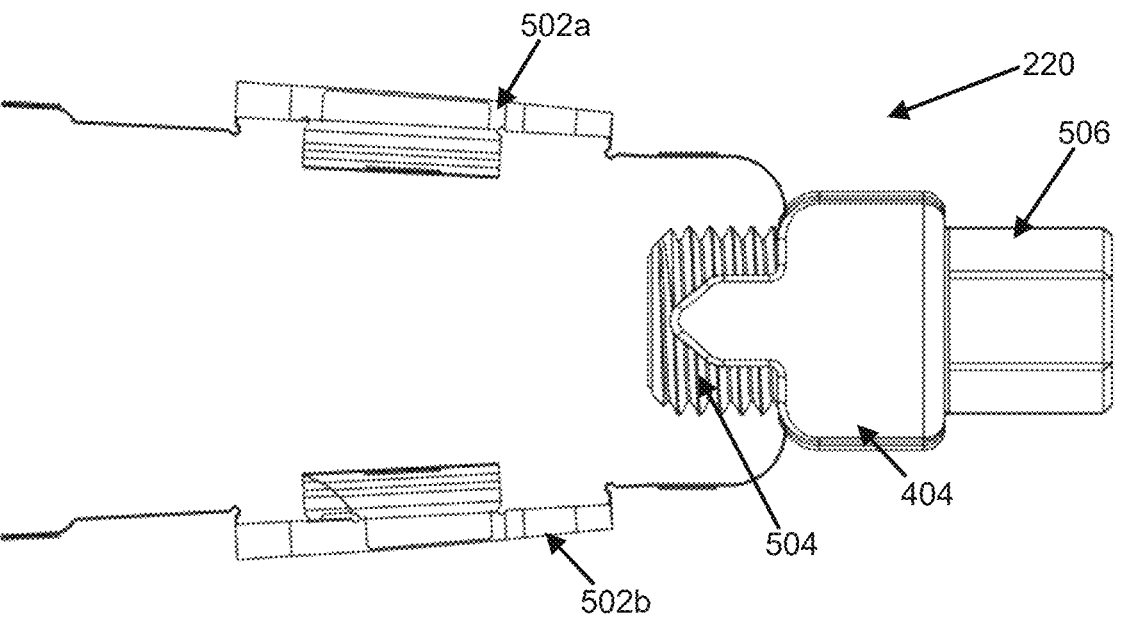

FIG. 6A-B illustrates the electronics module 404 and two carriers 502a-b that are integrated within the smart interbody spacer 220, according to some embodiments of the present disclosure.

Figure 7:
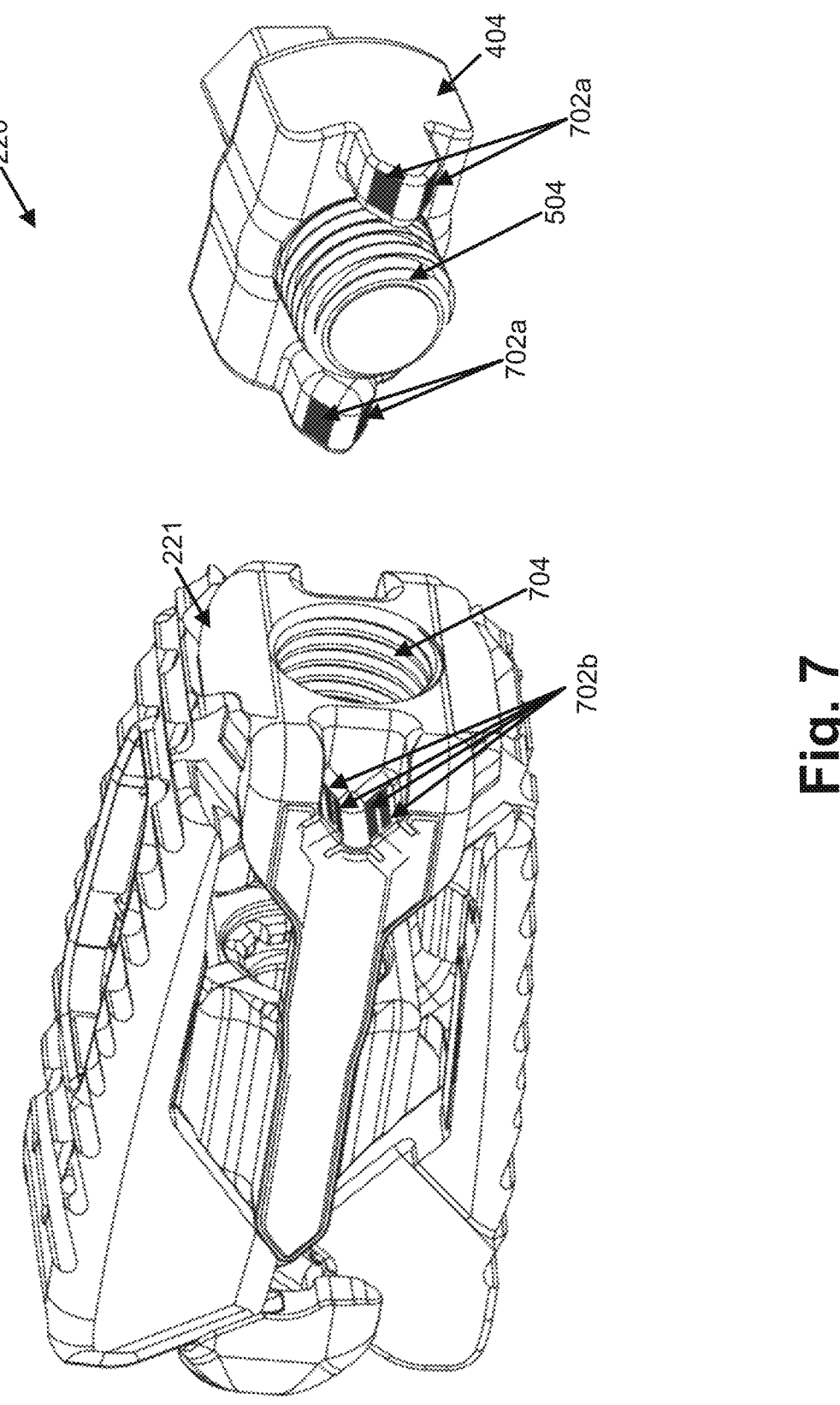
FIG. 7 illustrates the electronics module removed from the interbody spacer, according to some embodiments of the present disclosure.

FIG. 7 illustrates the electronics module removed from the interbody spacer, according to some embodiments of the present disclosure.

In some embodiments, the electrical circuitry within the electronics housing is configured to be removably attached to the interbody spacer through a screw that engages with a threaded hole of the interbody spacer.

According to some embodiments, as shown in FIG. 7, the carriers are part of the interbody assembly and the electronics module 404 (tether not shown) is a physically separate assembly that is attached intraoperatively after the interbody is placed. Mechanical connection between the electronics module and interbody is accomplished via a retained screw (attachment screw 504) that engages with a threaded hole 704 in the interbody structure 221. Electrical connection is enabled by conductive contacts 702a of the electronics module 404 and conductive contacts 702b of the interbody structure 221 that interface when the electronics module 404 is connected with the attachment screw 504. The conductive contacts of the electronics module 404 may allow for transmitting power from the electrical circuitry within the electronics module 404 to load sensors and electrodes of the interbody spacer. The conductive contacts may also allow for receiving at the electrical circuitry the obtained force measurement(s) from the load sensors and the obtained impedance measurement(s) from the electrodes.

For example, the electronics housing includes conductive contacts which conduct power from the electrical circuitry to the plurality of load sensors and the plurality of electrodes, and receive a load signal from load sensor(s) and an electrode signal from electrode(s).

This configuration may be advantageous to enable the surgeon to insert, expand, and backfill the interbody with a graft material without concern for the damaging or interfering with the electronics module 404 or the tether. An additional benefit may be that the attachment screw 504 in the electronics module assembly enables a moderate compression preload of the graft material within a graft window of the interbody, further enhancing tissue continuity and mechanically-induced osteogenesis. Lastly, there may be economic benefits to isolating the higher cost electronics to only a few SKUs that can attach to all interbody sizes of the same footprint as opposed to pre-assembling the electronics module to each unique implant SKUs during manufacturing.

Figure 8A:
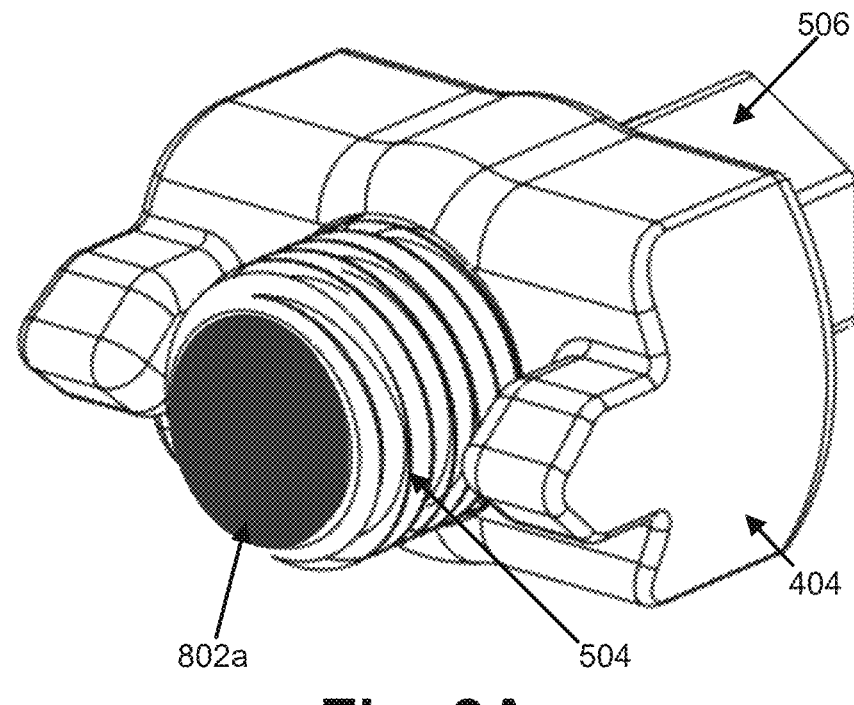
FIG. 8A illustrates the electronics module with a screw that includes an electrode, according to some embodiments of the present disclosure.

FIG. 8A illustrates the electronics module 404 with the attachment screw 504 that includes an electrode 802a, according to some embodiments of the present disclosure. The electrode may be located on an end of the screw opposite the end with the tether connector and drive feature 506, and the electrode 802a may be configured to obtain an impedance measurement indicating impedance of tissue surrounding the electrode 802a or a presence of biofilm surrounding the electrode 802a as discussed above. The electrode 802a may also be configured to generate an electrical field between the electrode 802a and another electrode (either on the electronics module 404 or somewhere else on the interbody spacer) to electrically stimulate a part of a body of a patient (that the implant is implanted within) adjacent the electrodes to a level which reduces biofilm or promotes bone growth.

Figure 8B:
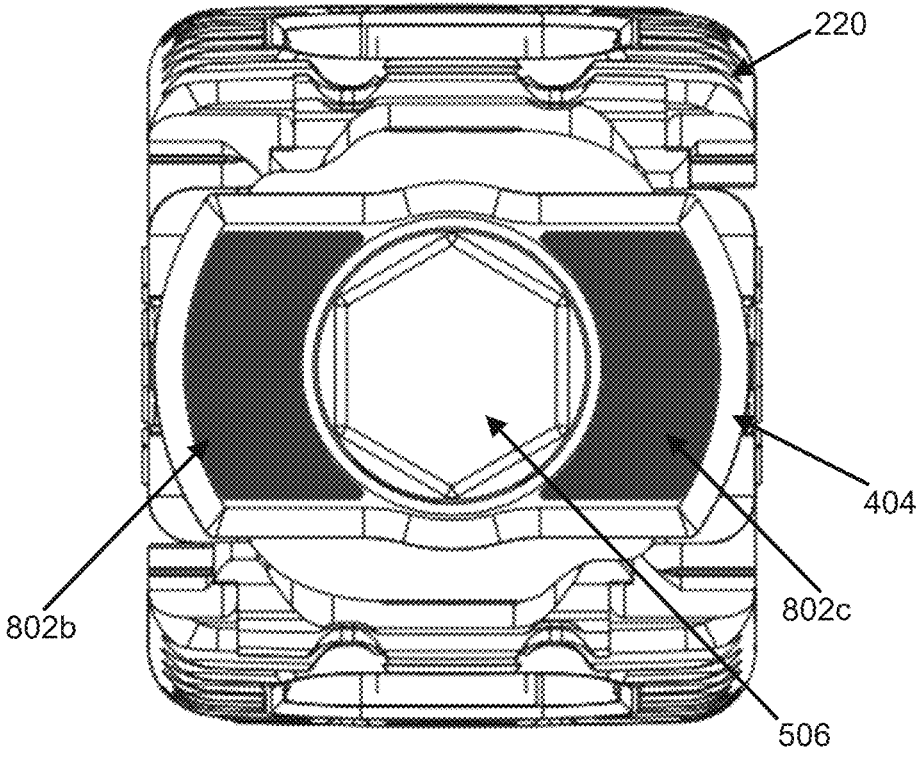
FIG. 8B illustrates the electronics module with electrodes on a surface of the electronics module, according to some embodiments of the present disclosure.

FIG. 8B illustrates the electronics module 404 with electrodes 802b-c on a surface of the electronics module 404, according to some embodiments of the present disclosure. In this example, the electrodes 802b-c are located on the back of the electronics module 404 and is configured to obtain an impedance measurement indicating impedance of tissue surrounding the electrodes 802b-c or a presence of biofilm surrounding electrodes 802b-c as discussed above. The electrodes 802b-c may also be configured to generate an electrical field between the electrodes 802b-c (or with other electrodes on the implant) to electrically stimulate a part of a body of a patient (that the implant is implanted within) adjacent the electrodes 802b-c to a level which reduces biofilm or promotes bone growth.

In these embodiments, the electronics module 404 includes three integrated electrodes 802a-c which, like all electrodes in the system, provide shared functionality for electrochemical sensing and electrical stimulation. While three electrodes are shown, it should be noted that any number of electrodes may be included on a surface(s) of the electronics module 404.

Figure 9A:
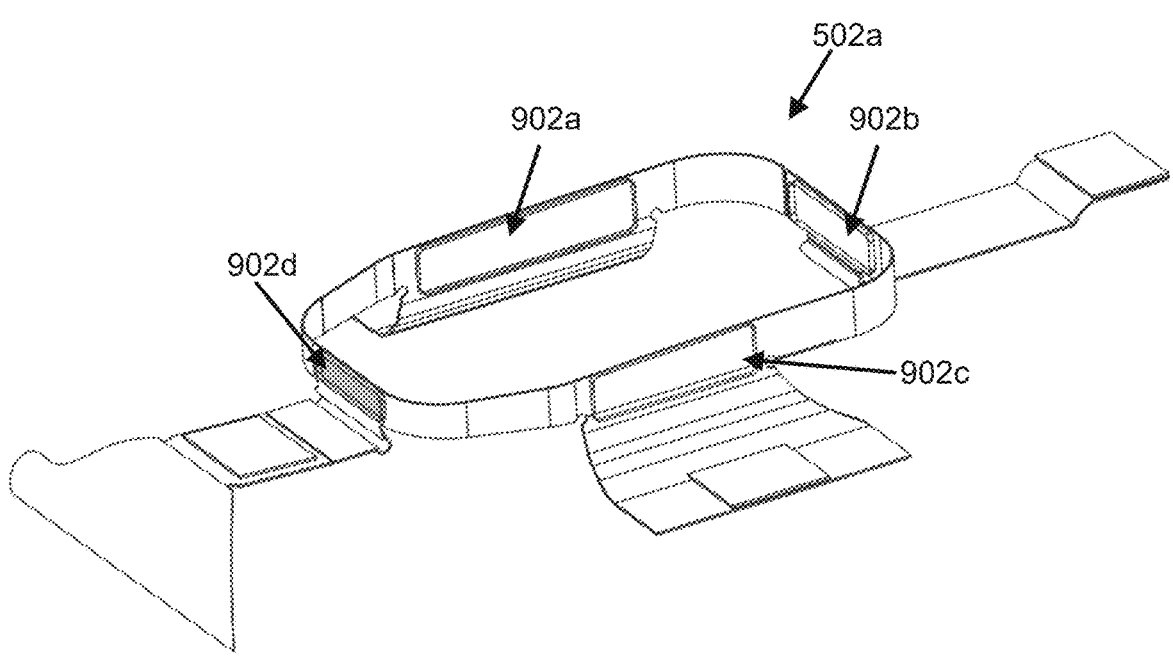
FIGS. 9A-B illustrates a carrier of the smart interbody spacer, according to some embodiments of the present disclosure.
Figure 9B:
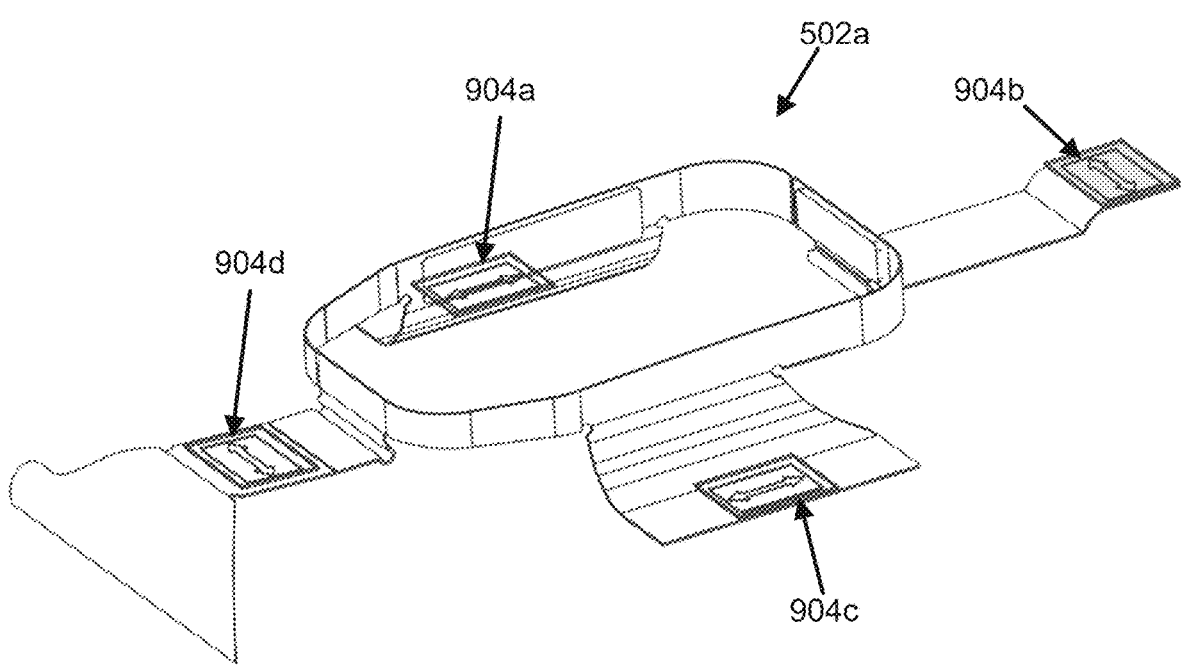

FIGS. 9A-B illustrates a carrier 502a of the smart interbody spacer, according to some embodiments of the present disclosure. While carrier 502a is shown in FIG. 9A-B, the other carriers of the interbody spacer may include the same or similar features as carrier 502a described herein.

The carriers may be designed to minimize susceptibility to mechanical damage of the electrical components during handling, simplify the assembly process during manufacturing, and minimize manufacturing costs by leveraging scalable, established production techniques. The endplate carrier 502a is shown below with the integrated interior electrodes 902a-d and load sensors 904a-d.

Figure 9C:
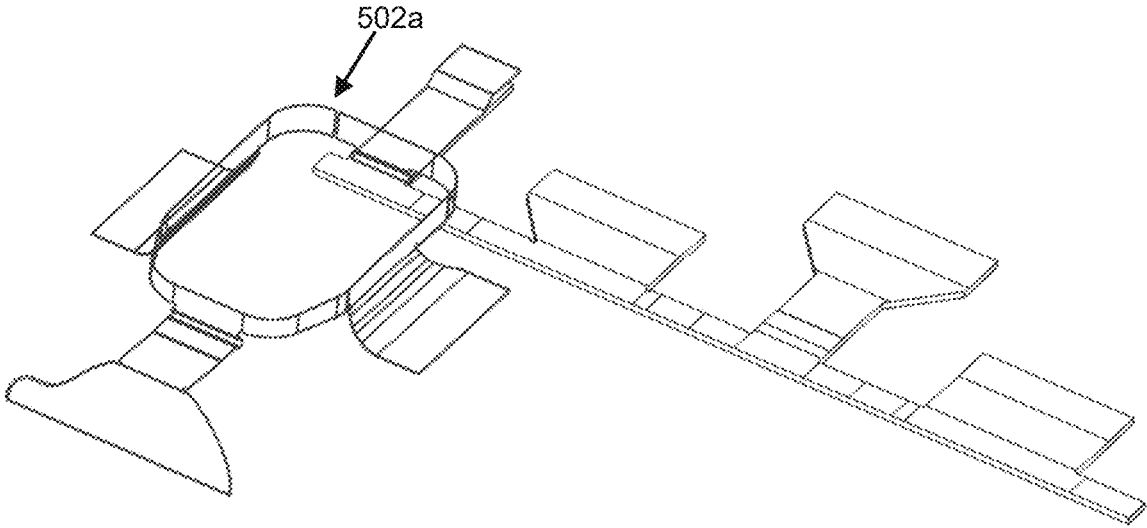
FIG. 9C illustrates the carrier of the smart interbody spacer in a two-dimensional and three-dimensional structure, according to some embodiments of the present disclosure.

FIG. 9C illustrates the carrier 504a of the smart interbody spacer in a two-dimensional and three-dimensional structure, according to some embodiments of the present disclosure.

Each endplate carrier may include load sensors 904b. For example, as shown in FIG. 9C, the endplate carrier may include four miniature linear strain gauges assembled to a flexible circuit. The load sensors 904a-d may receive power from the electrical circuitry in the electronics module 404 and obtain a force measurement of force exerted onto the load sensors of the interbody spacer.

While four load sensors are shown, it should be noted that the carriers may include any number of load sensors. Additionally, it should be noted that while strain gauges are used herein, any type of sensor capable of measuring forces may be used.

The base flexible circuit can be constructed two-dimensionally using flexible printed circuit board (flex PCB) manufacturing processes and later formed to the three-dimensional shape. As an added benefit, this design may take advantage of economies of scale by compactly nesting many circuit components within a single PCB panel.

Figure 9D:
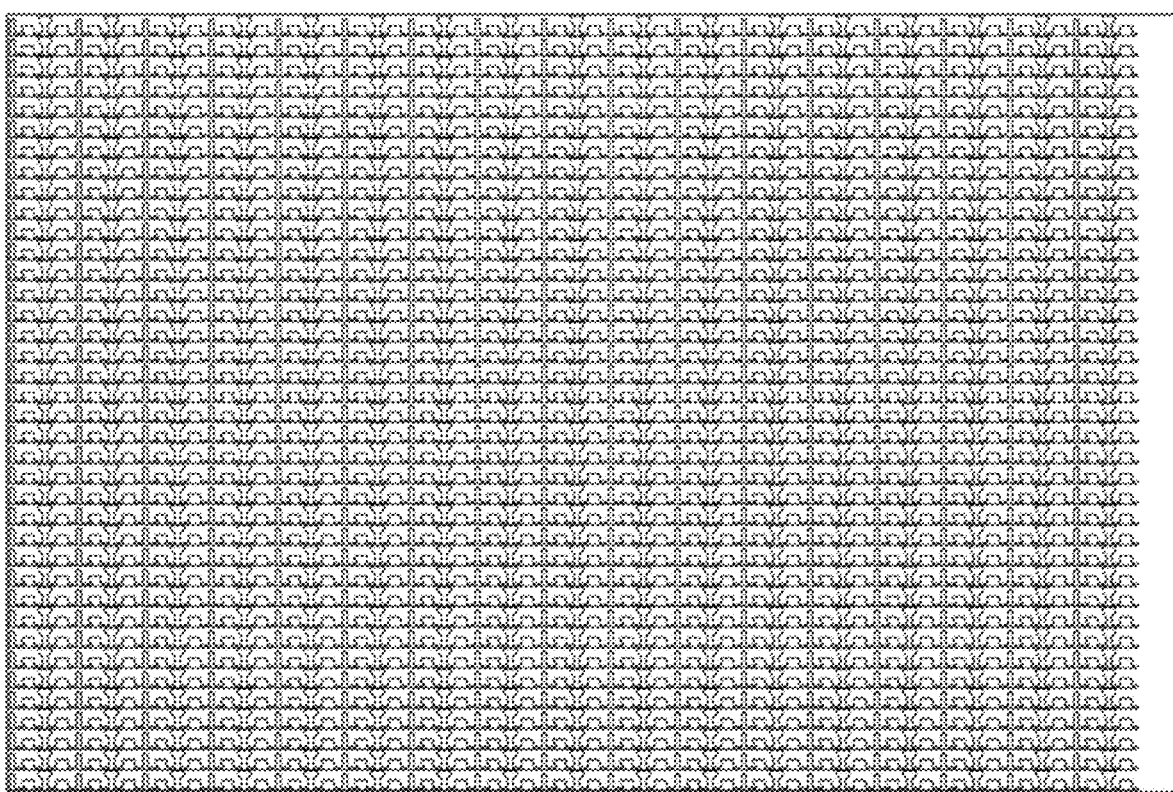
FIG. 9D illustrates a PCB panel with a plurality of carriers produced thereon, according to some embodiments of the present disclosure.

FIG. 9D illustrates a PCB panel with a plurality of carriers produced thereon, according to some embodiments of the present disclosure. In the example shown in FIG. 9D, 600+ endplate circuits can be produced from a single 12"×18" PCB panel.

Figure 10A:
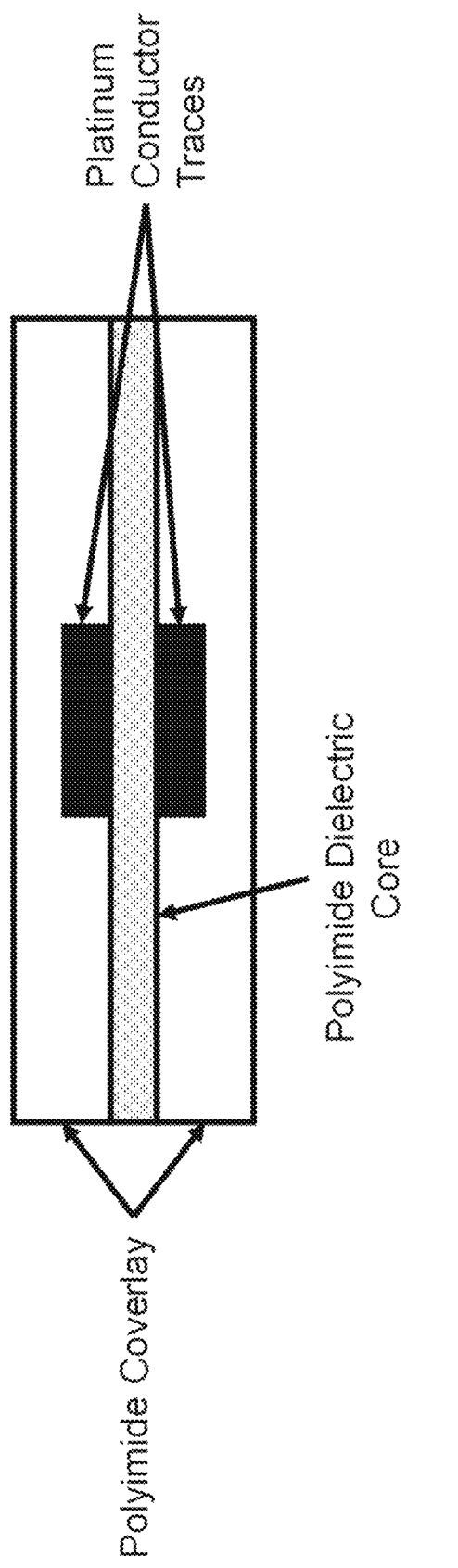
FIG. 10A illustrates a biocompatible 2-layer flex PCB construction, according to some embodiments of the present disclosure.

FIG. 10A illustrates a biocompatible 2-layer flex PCB construction, according to some embodiments of the present disclosure.

The flex PCB substrates may be natively biocompatible and include polyimide (PI), polyethylene terephthalate (PET), polytetrafluoroethylene (PTFE), and polyether ether ketone (PEEK). Copper intermediate layers may be avoided to preserve biocompatibility in the event of electrode corrosion or mechanical breakage of the carrier in situ. Instead, electrodeposition or adhesion of thin-films may be utilized to form the conductive traces from biocompatible noble metals such as platinum, gold, or silver.

Figure 11A:
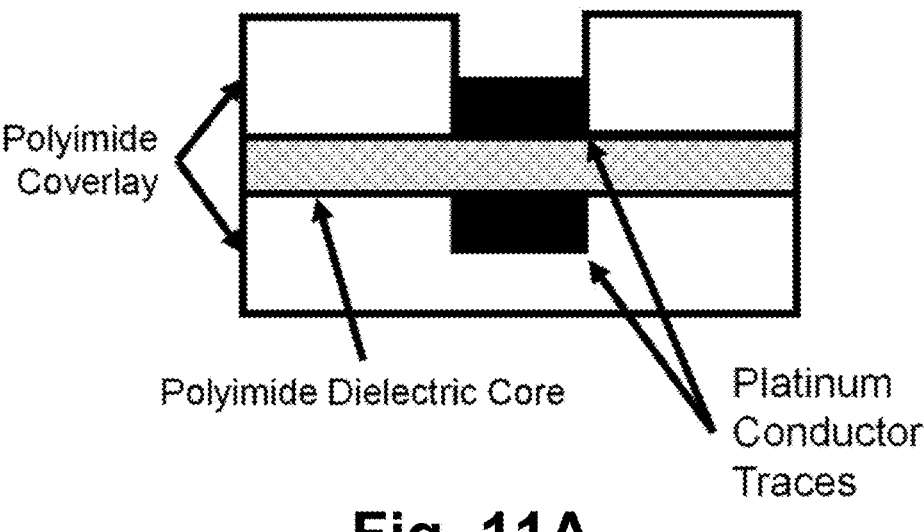
FIGS. 11A-C illustrate various constructions of functionalized electrodes, according to some embodiments of the present disclosure.
Figure 11B:
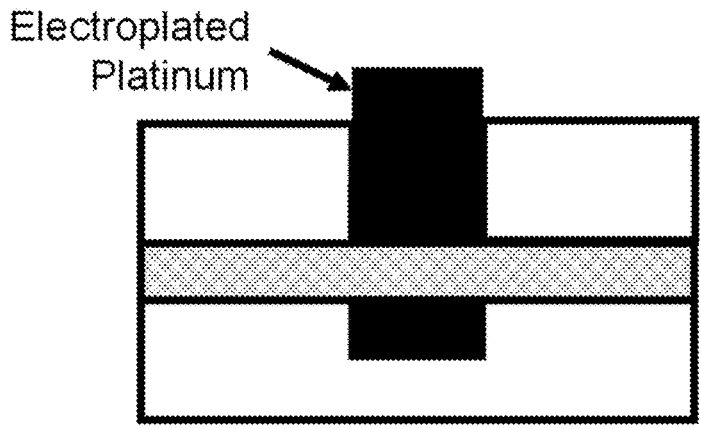
Figure 11C:
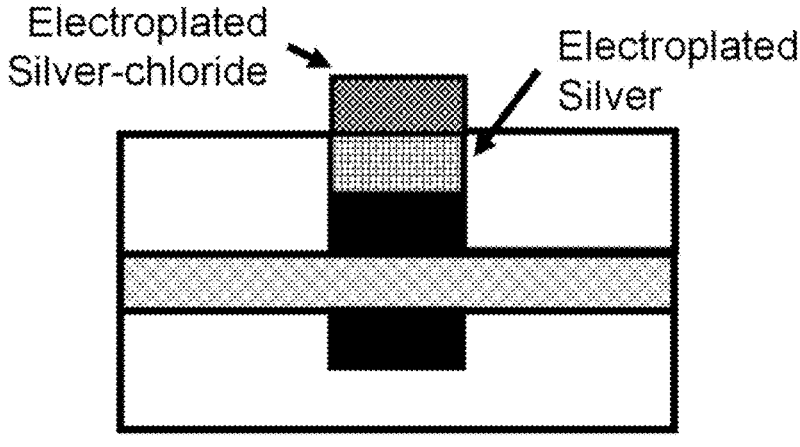

FIGS. 11A-C illustrate various constructions of functionalized electrodes, according to some embodiments of the present disclosure.

During manufacture of the flex PCB, the electrodes used herein may be functionalized for use as electrochemical sensors and stimulation electrodes. Functionalization of electrodes occurs by electroplating additional material onto the exposed electrode contacts. Platinum iridium may be used as a material for implantable stimulation electrodes, as shown in FIG. 11A, due to excellent biocompatibility, corrosion resistance, low noise, and electrical sensitivity. For example, a stimulation electrode of the interbody spacer and/or smart rod may include platinum conductor traces. In addition, one or more of the electrodes may be dedicated as a reference electrode by electroplating the electrode with a material that has a stable open circuit potential, as shown in FIG. 11B. Silver/silver-chloride may be used as a material for the reference electrodes in implantable electrochemical systems, as shown in FIG. 11C. To prepare a silver/silver-chloride (Ag/AgCl) reference electrode, a layer of silver is first electroplated onto the exposed platinum electrode pads. For example, a second electrode on the interbody spacer and/or smart rod may be functionalized as a reference electrode and include a silver or silver-chloride electroplating. Then, the silver surfaces are immersed in a chloride-rich solution, such as potassium chloride or sodium chloride, to form the silver-chloride layer.

In some embodiments, based on the functionalizing of a certain electrode, the electrical circuitry of the interbody spacer or smart rod operates the electrode as a stimulation electrode or as a reference electrode.

After the base flex PCB is created, the strain gauges can be assembled. Generally, the metal alloys embedded within strain gauges are not biocompatible. However, such devices can be rendered biocompatible and implantable via hermetic encapsulation, which helps to ensures that the non-biocompatible internal materials are isolated with an airtight seal from the external in vivo environment. For example, the plurality of load sensors and/or electrodes may be hermetically encapsulated on the carriers (or other parts of the implants) of the interbody spacer and the smart rod. Biocompatible materials for hermetic encapsulation of implantable electronics include parylene, glass, silicone, and PTFE. During the encapsulation process, feedthroughs may be incorporated to enable electrical connection of the strain gauge contacts with the mating contacts on the flex PCB. These feedthroughs might consist of gold solder preforms, which can be directly used to couple the strain gauge to the circuit. After the strain gauges are assembled to the circuit, a final encapsulation layer can be coated on the entire carrier assembly to provide environmental protection, prevent water absorption in the PI substrate, prevent delamination of the flex PCB layers, and serve as an additional biocompatibility barrier. In addition, this final encapsulation layer could be added after the carrier is formed into the 3D shape via fixturing. With a sufficiently stiff encapsulation material, the carrier could retain the 3D shape to assist in final assembly, which involves adhesion of the carrier to the titanium endplates using a biocompatible adhesive, such as cyanoacrylate (CA).

Although not explicitly detailed in this disclosure, the carriers (e.g., carriers 502c-d in FIGS. 5A-B) located on the sides of the interbody as well as the carriers (e.g., carrier 208a in FIG. 2) positioned on the smart rod can both be manufactured with the previously described processes. They may each include one or more electrodes on a surface of the carrier.

The tether 302 is discussed in further detail below.

Figure 12:
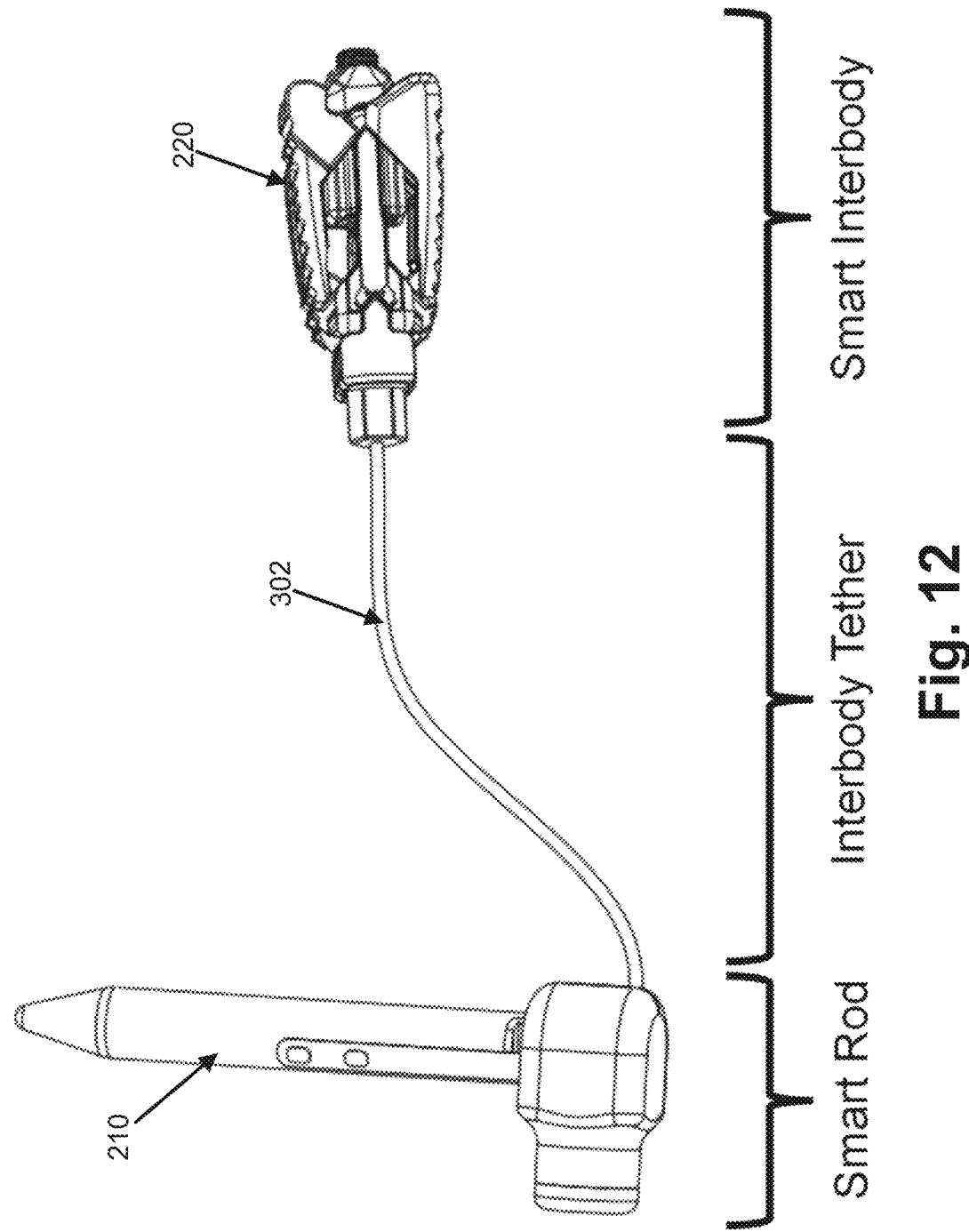
FIG. 12 illustrates the smart rod 210a and smart interbody spacer 220 connected through the tether 302, according to some embodiments of the present disclosure.

FIG. 12 illustrates the smart rod 210 and smart interbody spacer 220 connected through the tether 302, according to some embodiments of the present disclosure.

The ipsilateral portion of the implant construct, excluding the pedicle screws and locking caps, includes a smart rod 210, interbody tether 302, and smart interbody spacer 220. The tether 302 functions as a power and data link between the smart rod 210, which contains the wireless power and communication interface, and smart interbody spacer 220.

For example, the tether 302 may connect the electrical circuitry of the smart rod 210 to the electrical circuitry of the interbody spacer 220 and is configured to transfer power from the electrical circuitry of the smart rod 210 to the electrical circuitry of the interbody spacer 220. Additionally, the tether may be configured to transfer electrical signals from the electrical circuitry of the interbody spacer 220 to the electrical circuitry of the smart rod 210.

In some embodiments, the power may be transferred from the interbody spacer to the smart rod and the electrical signals from the smart rod to the interbody spacer.

The construction of the tether 302 may be similar to that of an electrode lead which includes an elastomeric tube (e.g. silicone) surrounding a bundle of biocompatible, and insulated wires (e.g. PTFE-coated titanium). The compliance and low-friction qualities of the lead structure allow the tether 302 to be safely routed through the surgical corridor without risk of harm to the traversing or exiting nerve roots. Additionally, the elastomeric material that forms the tube may be loaded with about 30% carbon nanotubes by volume to provide shielding to reduce electromagnetic interference (EMI). Further, the carbon nanotubes may enhance the elastomeric material with conductive properties, which may enable stimulation of an exterior of the tether 302 to prevent and reduce biofilm formation.

For example, the electrical circuitry of the smart rod or the interbody spacer may be electrically coupled to a tether electrode that is coating at least a major length of an exterior surface of the tether and is configured to generate an electrical field through the tether electrode. The tether electrode that is coating a portion of the exterior surface may include carbon nanotube(s), as described above.

The tether 302 may be beneficial for efficient and reliable delivery of power to the deeply implanted smart interbody spacer 220. The intensity of wireless power is inversely proportional to the square of the distance from the source (i.e. transmitter on the skin) to the receiver (i.e. smart implant). Therefore, if the interbody is implanted twice as deep as the rod (e.g. 100 mm vs 50 mm), the transmitter must output 4 times as much power for the interbody and rod to receive equivalent power. Further, additional losses would be uniquely encountered when attempting to wirelessly power the interbody spacer due to interference from the posterior fixation implants and vertebral bodies as well as coupling inefficiencies caused by challenges targeting the deeply implanted coil with the external transmitter. The transmitter power could be increased to account for these losses, however, the transmitter power may be capped at a threshold that is relatively low level to avoid exposing the intermediate tissue to harmful amounts of radiation. In some embodiments, the threshold is a safety threshold called specific absorption rate (SAR) and is mandated by the FCC and FDA. With these considerations, the tether 302 offers a safe and effective means of delivering power and data to the interbody spacer while only requiring wireless transfer with the more superficial and accessible smart rods.

The smart rod is discussed in further detail below.

Figure 13:
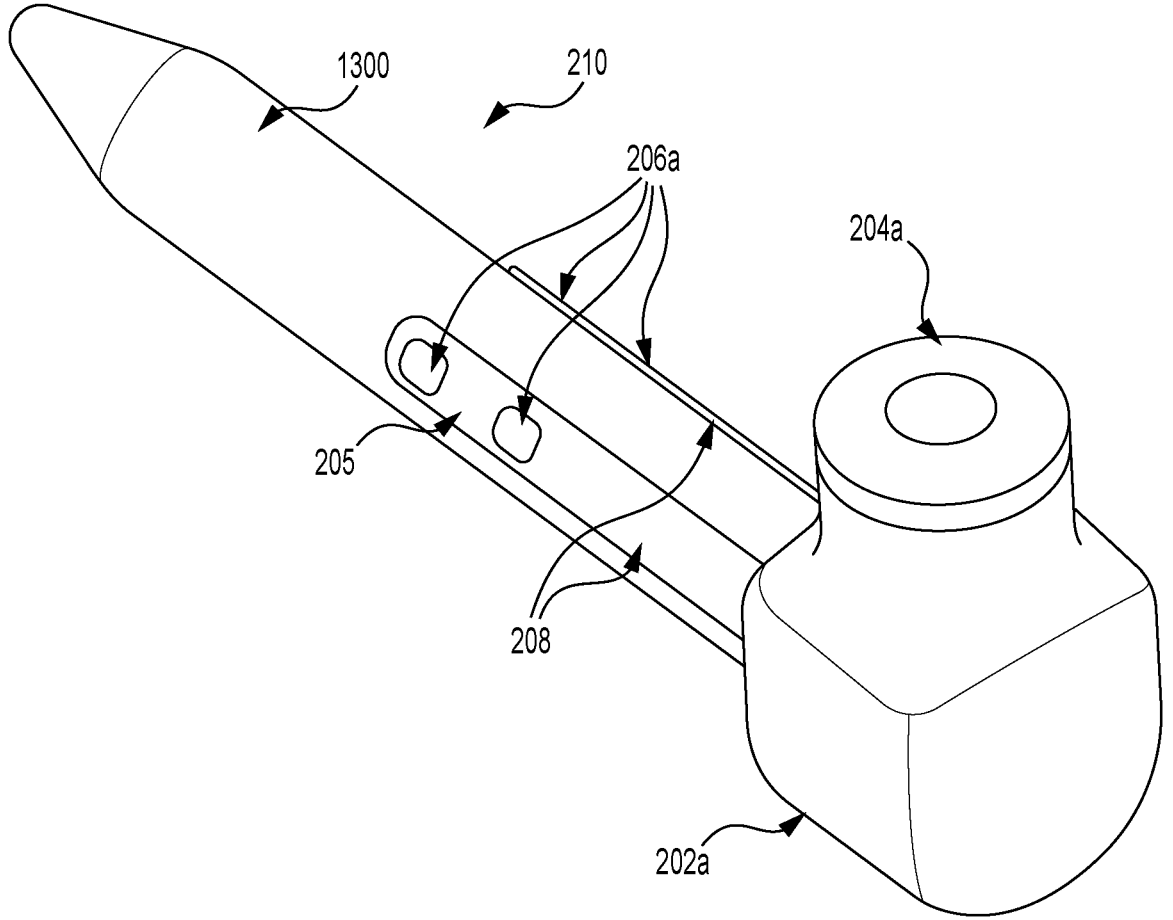
FIGS. 13-14 illustrate the smart rod 210a including electrodes 206a and load sensors 205, according to some embodiments of the present disclosure.
Figure 14:
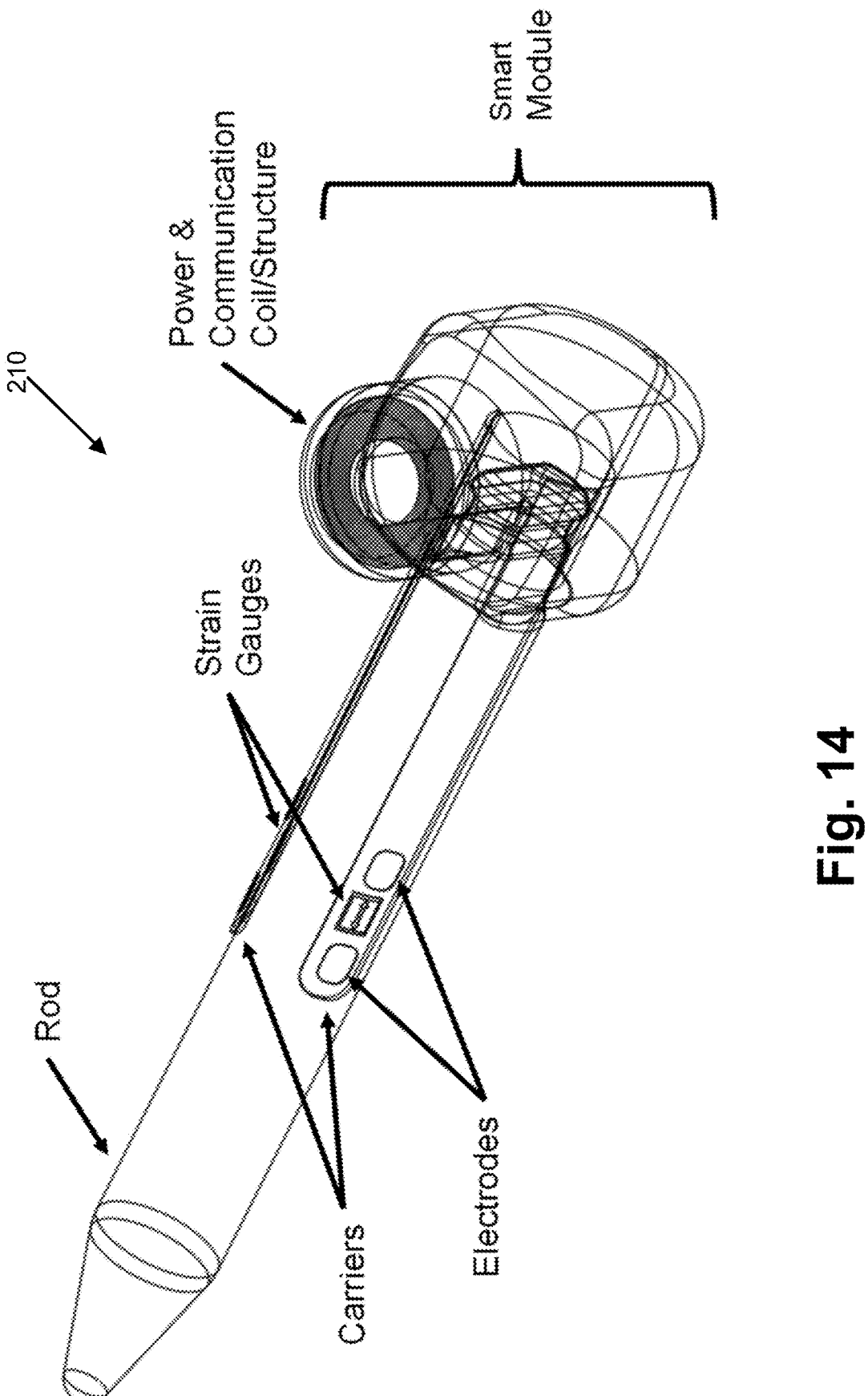

FIGS. 13-14 illustrate the smart rod 210 including electrodes 206a and load sensors 205, according to some embodiments of the present disclosure. It should be noted that smart rods 210a-b may include the same or similar features of smart rod 210 discussed herein.

The smart rod 210 may enable in situ bone growth stimulation, fusion monitoring, infection detection, and biofilm eradiation within the posterior column in a form factor that is minimally invasive to adjacent tissues and minimally disruptive to established workflows. The smart rod 210 may be optimized for a one-level MIS TLIF procedural solution and include a 5.5 mm diameter titanium curved rod 1300 in 30-55 mm lengths in 5 mm increments. The smart rod 210 may also include the integrated intelligent healing system (discussed above) including several subsystems including electrochemical sensing, electrical stimulation, strain sensing, temperature sensing, and motion sensing. In some embodiments, the smart rod 210 includes a wireless power and communication interface 204a that enables the smart rod 210 to exchange power and data with an external wearable device. Additionally, the ipsilateral smart rod 210 exchanges power and data with the smart interbody (e.g., smart interbody spacer 220) via the interbody tether (e.g., tether 302). The smart rod also include the electronics module 202a (also referred herein as a smart module).

For example, the temperature sensing may be enabled by a temperature sensor within the electronics module 202a or electrically connected thereto. The temperature sensor may be configured to receive power from the electrical circuitry within the electronics module 202a and provide a temperature measurement signal to the electrical circuitry.

FIGS. 15A-C illustrates the smart rod 210 fully assembled in FIGS. 15A-B and removed from the rod 1300 in FIG. 15C, according to some embodiments of the present disclosure.

In some embodiment, the carriers 208 of the smart rod 210 are part of the smart rod assembly and the electronics module 202a is a physically separate assembly attached intraoperatively prior to implantation. The electrical circuitry within the electronics housing may be configured to be removably attached to the implant rod through a retained screw that engages with a threaded hole in a proximal end of the implant rod. For example, mechanical connection between the electronics module 202a and rod 1300 may be accomplished via a retained screw that engages with a threaded hole in the proximal end of the rod 1300. The electrical housing of the smart rod may include conductive contacts which conduct power from the electrical circuitry to the plurality of electrodes and to receive load signal(s) and electrode signal(s). electrical connection may be enabled by conductive contacts that interface the electronics module 202a to the electrode(s) and load sensor(s) when the electronics module 202a is connected to the rod 1300 via the attachment screw. This configuration may be advantageous to isolate the higher cost electronics to only two SKUs (ipsilateral with tether connector and contralateral without tether connector) that can attach to all rod sizes as opposed to pre-assembling the electronics module to each of the unique implant SKUs during manufacturing.

The external device is discussed in further detail below.

Figure 16:
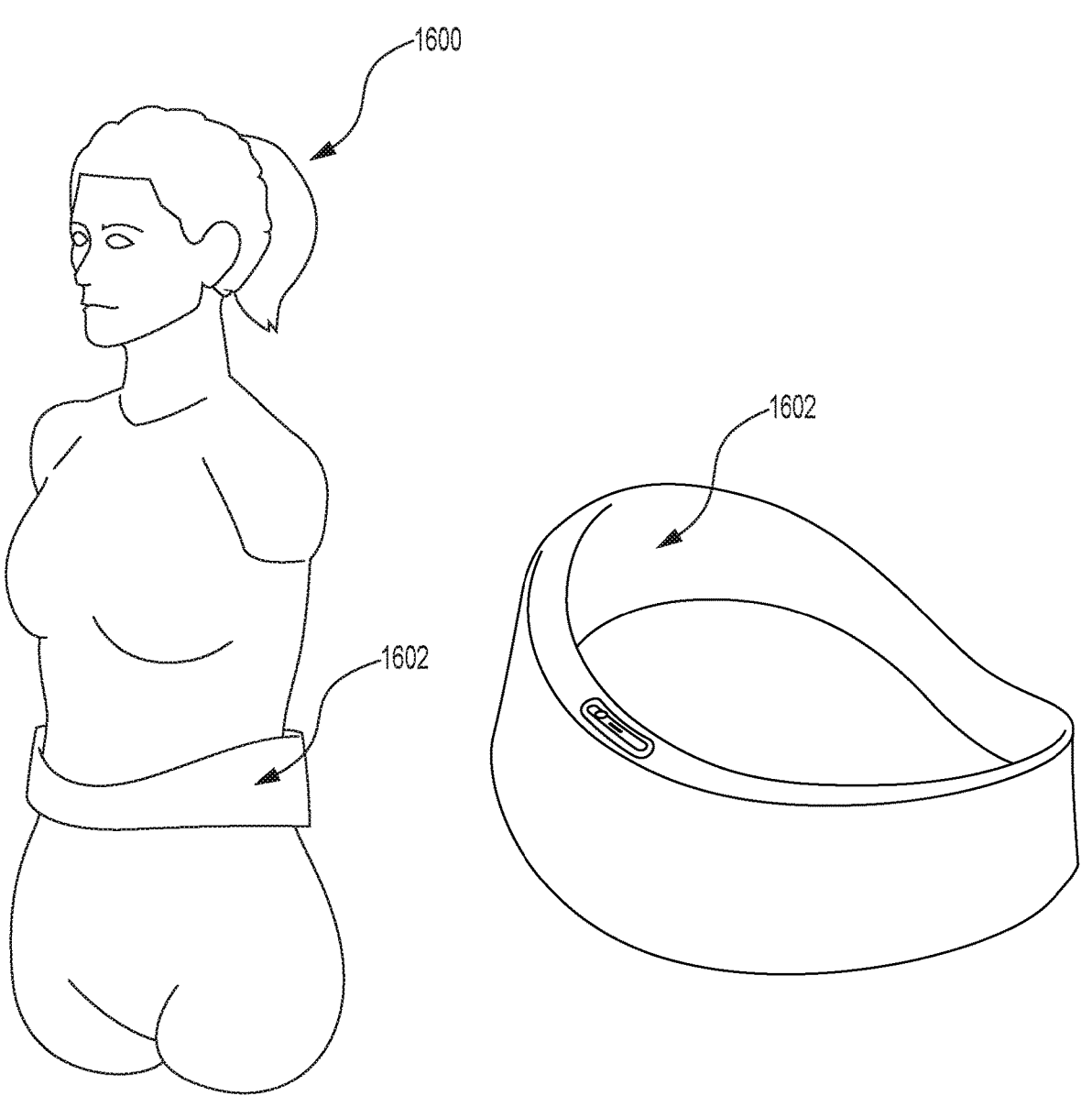
FIG. 16 illustrates a patient wearing the external device, according to some embodiments of the present disclosure.
Figure 17:
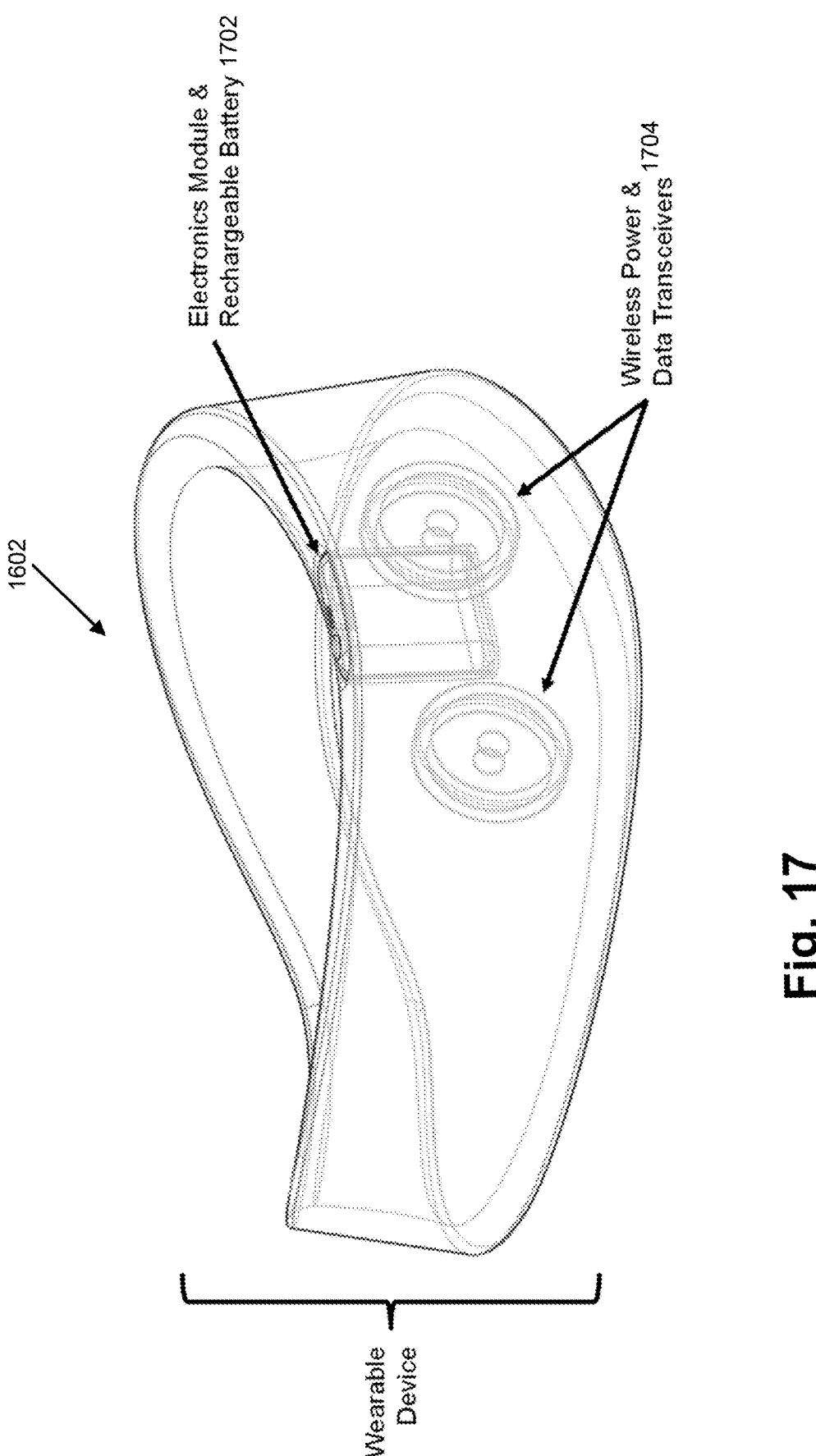
FIG. 17 illustrates the external device, according to some embodiments of the present disclosure.

FIG. 16 illustrates a patient 1600 wearing the external device 1602, according to some embodiments of the present disclosure. FIG. 17 illustrates the external device 1602, according to some embodiments of the present disclosure.

The external device 1602 may include a wearable housing that holds an electronics module and rechargeable batter 1702 that is connected to wireless power and data transceivers 1704. The external device may remain outside the body of the patient and is not implanted within the body of the patient. It should be noted that while the external device includes a rechargeable battery, the external device may alternatively include a wire for plugging into a physically separate power supply.

The smart implants (e.g., smart rod 210) is wirelessly coupled (through the wireless power and data transceiver 704) with the external device 1602, such as a wearable lumbar brace shown in these figures, via resonant inductive coupling. The inductive coupling link (e.g. 6.8 MHz) enables the wireless power and data transceiver 1704 to deliver power to the wireless power and communication interface of the smart rod and facilitates bidirectional communication between the internal and external components (i.e., the transceiver of the external device may function as a receiver too). The external device is designed to deliver sufficient continuous power from the electronics module and rechargeable battery 1702 to the implants (e.g., smart rod and/or smart interbody spacer) to eliminate the need for an intermediate rechargeable battery (i.e., a battery within the implants). In some embodiments, the user attaches/wears the external device 1602 at specified times (e.g. 1 hour per week), which enables the smart implants to receive power and perform their clinical sensing and treatment functions. This configuration avoids the need for implanted primary or rechargeable batteries in the implants and provides the patient with greater agency over their treatment, data, and privacy.

Figure 18:
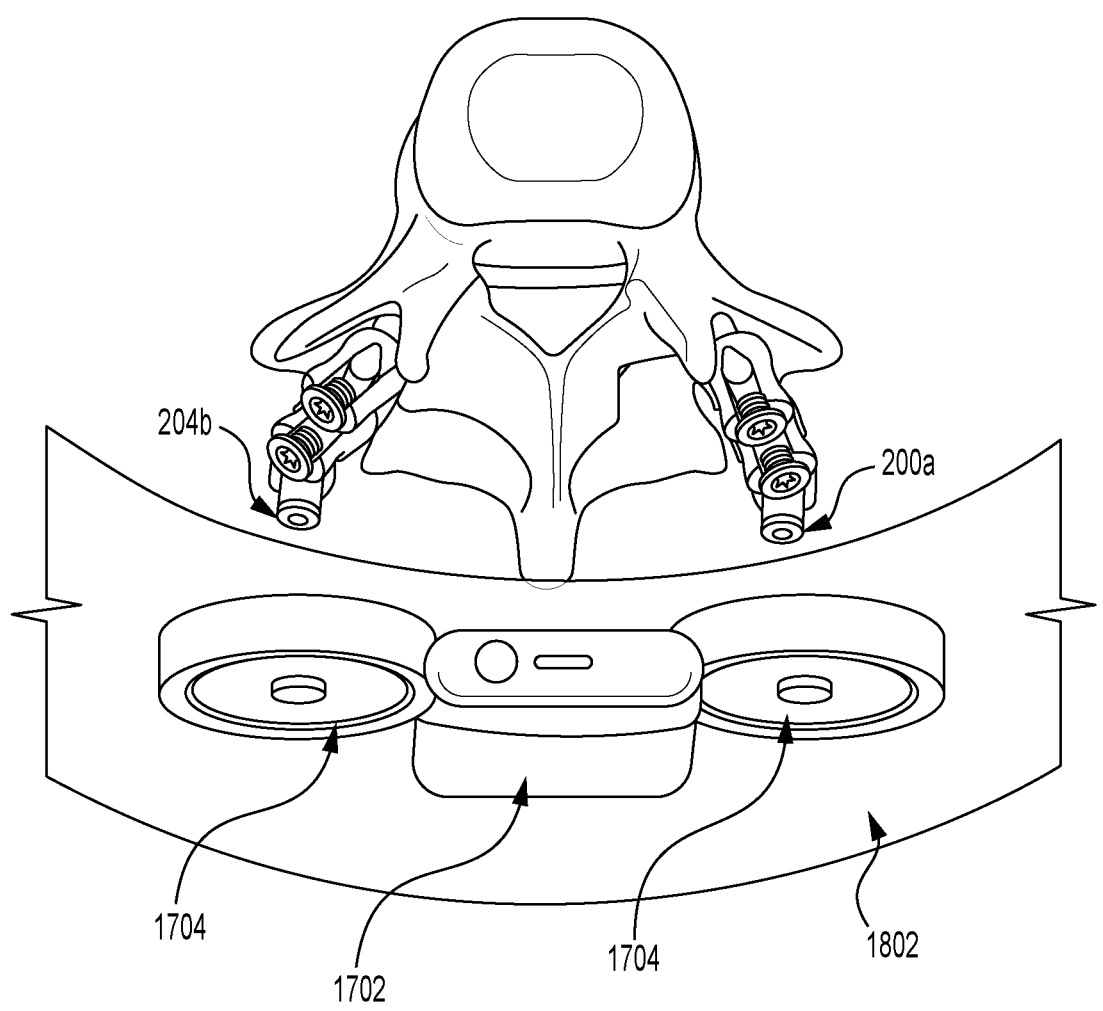
FIG. 18 illustrates a view of the external device worn by the patient communicating with the smart rods, which is connected to a cloud, according to some embodiments of the present disclosure.
Figure 19:
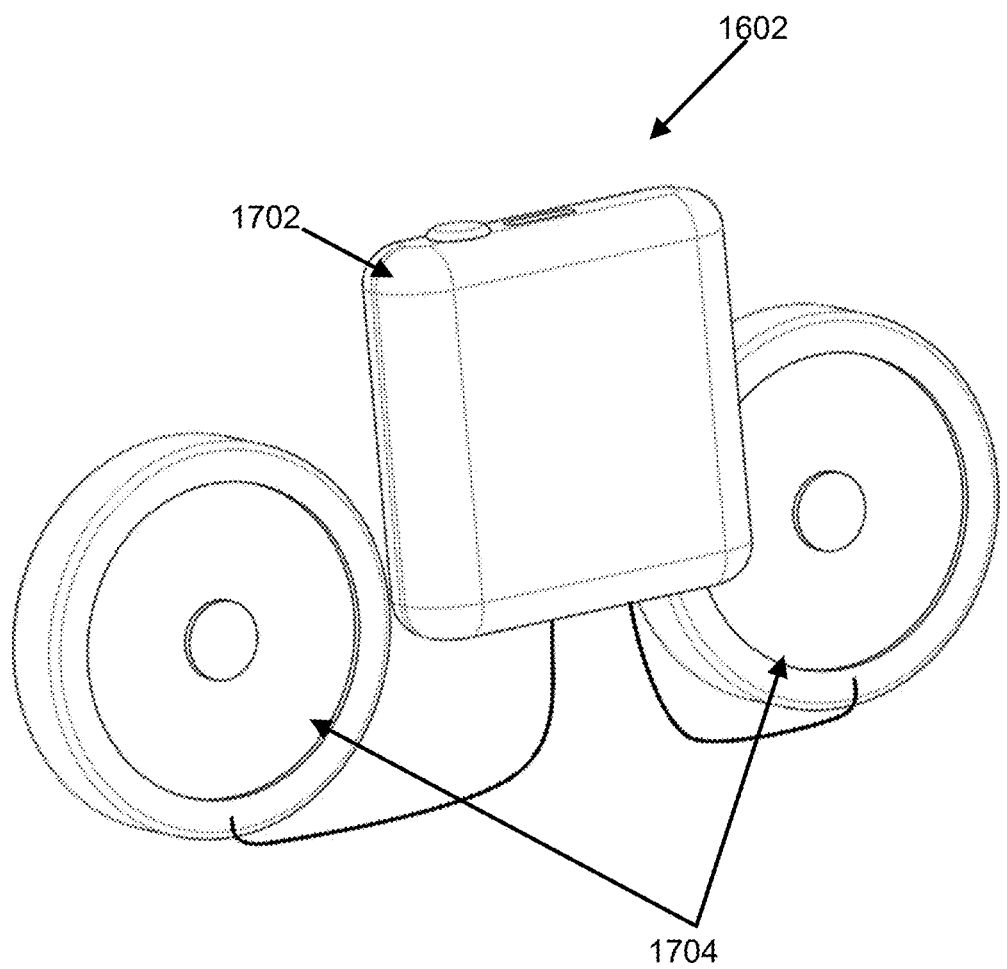
FIG. 19 illustrates the external device without a housing, according to some embodiments of the present disclosure.

FIG. 18 illustrates a view of the external device worn by the patient communicating with the smart rods, according to some embodiments of the present disclosure. FIG. 19 illustrates the external device without a housing, according to some embodiments of the present disclosure.

The wearable device consists of one or more wireless power and data transceivers 1704 (e.g. inductive coils), an electronics module and rechargeable battery 1702, and the housing 1802. In the Figures herein, the housing 1802 is a lumbar brace, however, the housing 1802 could be of a different form factor, such as a lumbar bolster, or be removed entirely. In the latter scenario, the transceivers 1704 could be adhered to the skin in the lumbar region and the electronics module and rechargeable battery 1702 could be placed in the patient's pocket (not shown).

The electronics module and rechargeable battery 1702 facilitates the distribution of energy from the rechargeable battery pack to the wireless power and data transceivers 1704. The electronics module of the external device may also include a separate 2.4 GHz wireless communication module capable of communicating with a patient's smart phone (or other user device) via Bluetooth or patient's home internet router via WIFI. In addition, this 2.4 GHz module can also be used by the clinician to communicate with the wearable and implants during follow-up visits.

In some embodiments, the electrical circuitry of the smart rod is configured to transfer power received from the external device through the wireless power and communication interface to the plurality of components (e.g., the load sensors and/or electrodes) while the wireless power and communication interface is receiving power from the external device.

Figure 20:
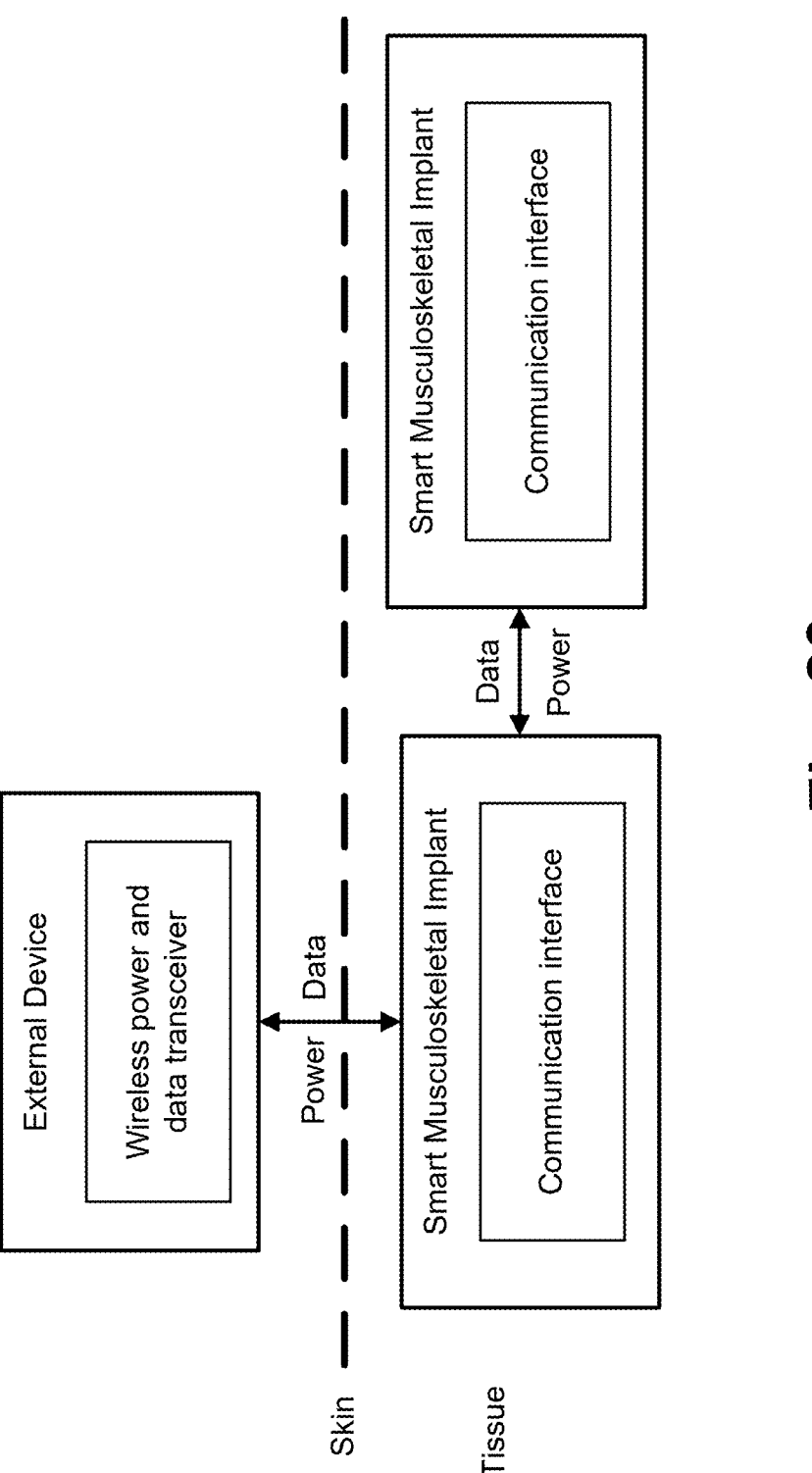
FIGS. 20-22 illustrate communication between the external device and implanted smart implants, according to some embodiments of the present disclosure.
Figure 21:
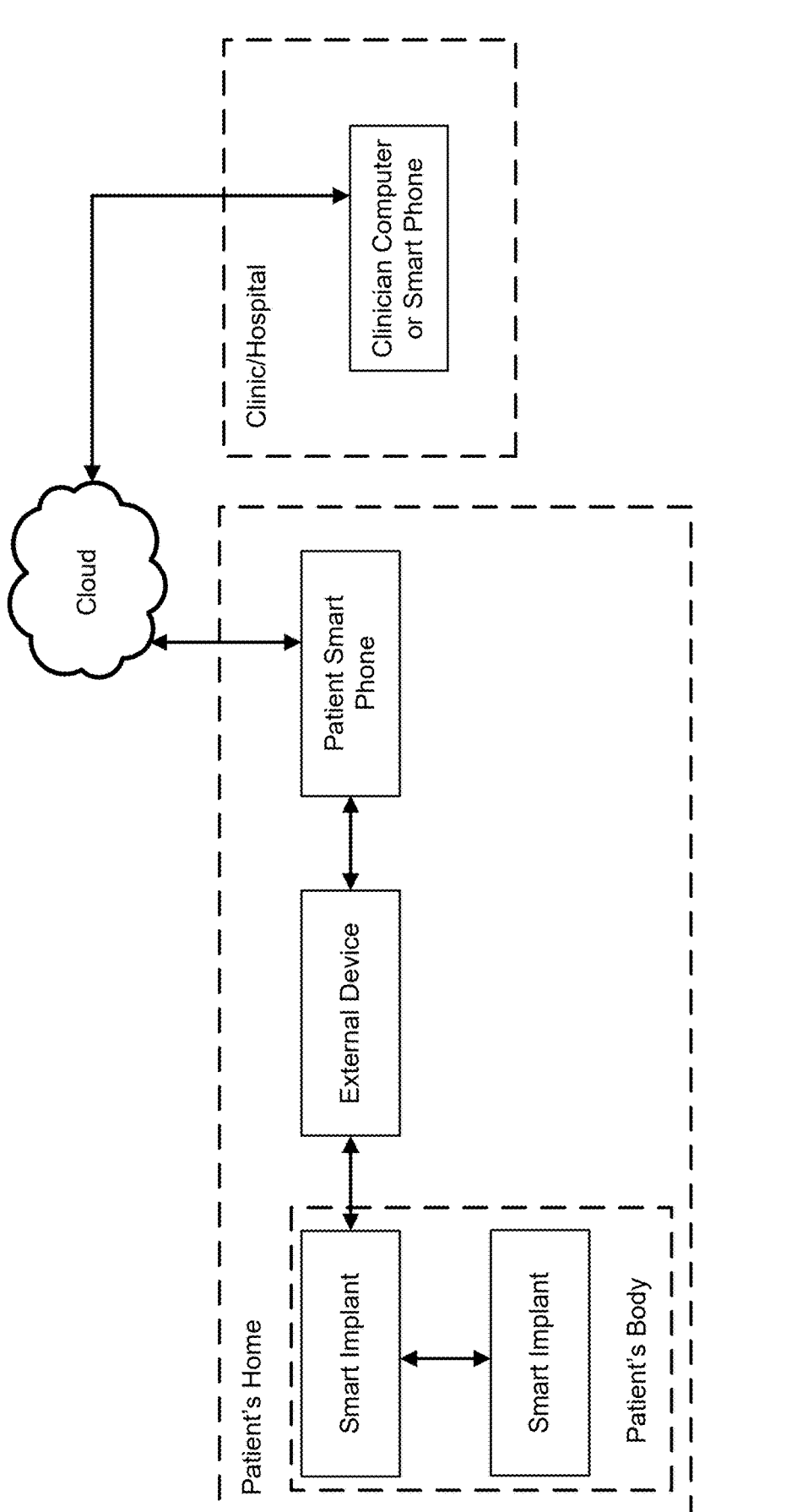
Figure 22:
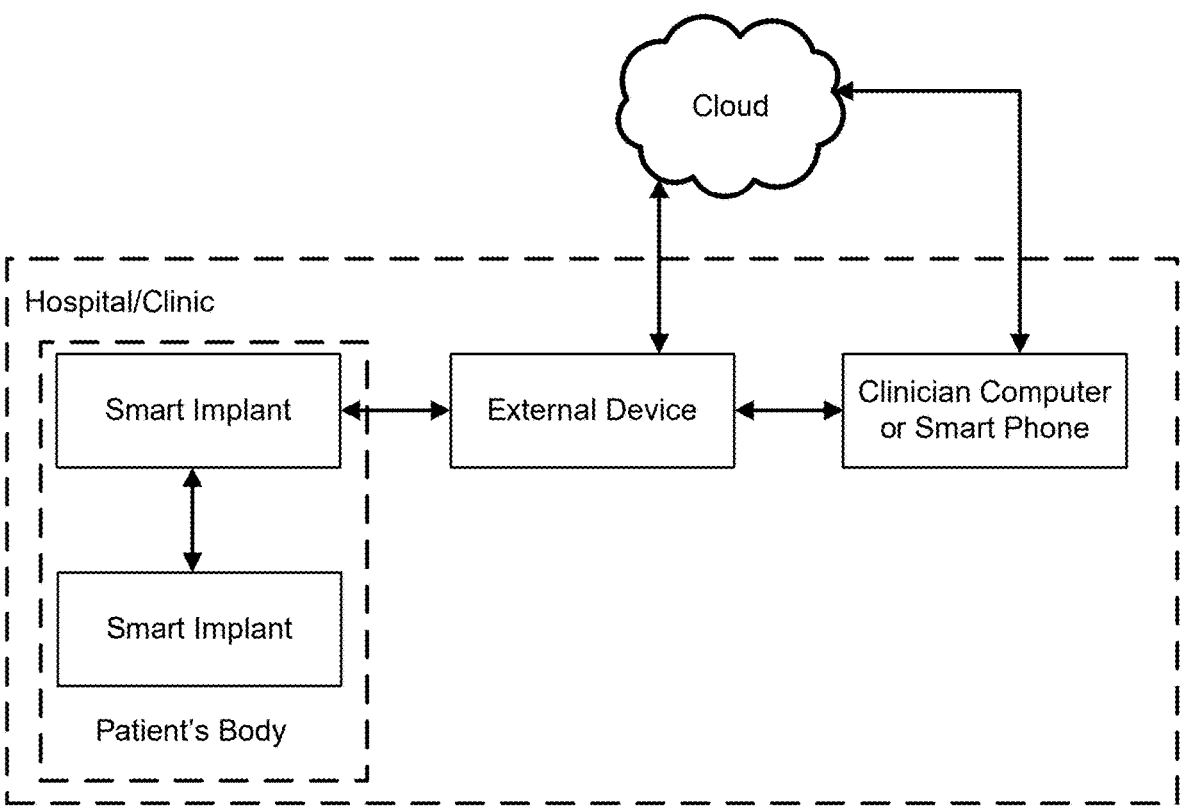

FIGS. 20-22 illustrate communication between the external device and implanted smart implants, according to some embodiments of the present disclosure.

The external device (e.g., external device 1602) may wirelessly transmit power and/or data from a wireless power and data transceiver to a smart implant (e.g., smart rod 210) through the smart implants communication interface. The power and/or data may further be transmitted from the smart implant through a tether, connecting the smart implant to another smart implant, to another smart implant (e.g., smart interbody spacer 220). The data from the external device to the smart implant(s) may include at least one of an instruction to one or both of the smart implants to generate an electrical field between at least two electrodes of the respective smart implant to a specified level that includes at least one of a current amplitude, frequency, pulse profile, pulse duration, and total treatment duration; an instruction to obtain and/or provide the force measurement through a plurality of load sensors of the smart implant; and an instruction to obtain and/or provide an impedance measurement through a plurality of electrodes of the smart implant. The power transmitted to the smart implant(s) may be used to power the smart implant(s) when receiving the power from the external device.

For example, the electrical circuitry of the interbody spacer or the smart rod may transfer power to different electrical components (e.g., load sensors and/or electrodes) while a wireless power and communication interface is receiving power from the external device.

The smart implant(s) may also transmit power and/or data to the external device. The external device may transmit the data to the patient's phone (or other user device, for example, a laptop, tablet, etc.). From the patient's phone the data may be transmitted through a cloud network and to a clinician device (e.g., clinician computer or smart phone). Data may also be transmitted the other direction to the smart implant(s) from the clinician device. Alternatively, the smart implant(s) may communicate data with the external device (1602) and then the data is transmitted from the external device through the cloud network and to the clinician device. This may provide the benefit of communicating measurements from the smart implant(s) to the patient or clinician and allow the clinician to communicate instructions to the smart implants for treatment (promote bone growth or reduce biofilm) or for further measurement readings.

In an example, the external device may transmit a message to the smart rod. The electrical circuitry of the smart rod, through the wireless power and communication interface of the smart rod, may be configured to receive the message from the external device. The message may include an instruction to generate an electrical field according to an instructed electrical field characteristic that includes at least one of a current amplitude, frequency, pulse profile, pulse duration, and total treatment duration for the electrical field. The instructed electrical field characteristic may be specified by a clinician that sent the message via a clinician device to the external device, for transmission to the smart rod.

In some embodiments, the message may be intended from the clinician device to be transmitted to the interbody spacer. In these embodiments, the clinician device transmits the message to the external device and the external device transmits the message to the smart rod. The smart rod may be configured to transfer the message from the electrical circuitry of the smart rod to the electrical circuitry of the interbody spacer through the tether. The interbody spacer may be configured to receive the message through the tether that includes an instruction to generate the electrical field between at least two electrodes of the interbody spacer according to the instructed electrical field characteristic that includes at least one of a current amplitude, frequency, pulse profile, pulse duration, and total treatment duration.

What is claimed is:

1. An interbody spacer configured for implantation between spinal vertebrae, the interbody spacer comprising:
    electrical circuitry within an electronics housing of the interbody spacer;
    a plurality of load sensors spaced apart on carriers of the interbody spacer, the plurality of load sensors electrically connectable to the electrical circuitry and configured to
    receive power from the electrical circuitry, and
    provide to the electrical circuitry a load signal indicative of a measurement of force exerted onto the plurality of load sensors of the interbody spacer; and
    a plurality of electrodes spaced apart on a surface of the interbody spacer, the plurality of electrodes electrically connectable to the electrical circuitry and configured to receive power from the electrical circuitry, and
    at least one of
        provide to the electrical circuitry an electrode signal indicative of an impedance measurement indicating impedance of biological materials surrounding the plurality of electrodes or a presence of biofilm surrounding the plurality of electrodes, and
        generate an electrical field between at least two electrodes of the plurality of electrodes to electrically stimulate biological materials adjacent the at least two electrodes to a level which reduces biofilm or promotes bone growth,
    wherein the interbody spacer comprises an upper endplate, a lower endplate and an actuation mechanism configured to move the upper endplate and the lower endplate away from one another
    wherein the electrical circuitry within the electronics housing is configured to be removably attached to the interbody spacer through a screw that engages with a threaded hole of the interbody spacer.

2. The interbody spacer of claim 1, wherein the electronics housing includes conductive contacts which conduct power from the electrical circuitry to the plurality of load sensors and the plurality of electrodes, and receive the load signal and the electrode signal.

3. The interbody spacer of claim 1, further comprising:
    a temperature sensor configured to receive power from the electrical circuitry and to provide a temperature measurement signal to the electrical circuitry.

4. The interbody spacer of claim 1, wherein the electrical circuitry is configured to generate the electrical field between the plurality of electrodes as cathodic-biased current pulses.

5. The interbody spacer of claim 1, further comprising:
    a tether connecting the electrical circuitry of the interbody spacer to another electrical circuitry of an implant rod, wherein the tether is configured to transfer power from the another electrical circuitry of the implant rod to the electrical circuitry of the interbody spacer, and the tether is configured to transfer electrical signals from the electrical circuitry of the interbody spacer to the another electrical circuitry of the implant rod.

6. The interbody spacer of claim 5, wherein the electrical circuitry of the interbody spacer is configured to receive a message through the tether from the another electrical circuitry of the implant rod which includes an instruction to generate the electrical field between the at least two electrodes according to an instructed electrical field characteristic that includes at least one of a current amplitude, frequency, pulse profile, pulse duration, and total treatment duration.

7. The interbody spacer of claim 5, wherein the electrical circuitry of the interbody spacer is electrically coupled to a tether electrode coating at least a major length of an exterior surface of the tether and configured to generate an electrical field through the tether electrode.

8. The interbody spacer of claim 1, wherein the electrical circuitry of the interbody spacer is electrically coupled to a conductive screw that is physically attached to the interbody spacer, wherein the electrical circuitry of the interbody spacer is configured to generate an electrical field between the conductive screw and an electrode of the plurality of electrodes.

9. The interbody spacer of claim 1, wherein the plurality of electrodes are spaced apart on the surface of the interbody spacer forming one or more of:
    a surface of one or more of the carriers of the interbody spacer that is connected to the upper endplate or the lower endplate of the interbody spacer;
    a surface of one or more of the carriers that is connected to the electronics housing and extends along a side of the interbody spacer;
    a surface of the electronics housing; and
    a surface of a screw that connects the electronics housing to the interbody spacer.

10. The interbody spacer of claim 1, wherein a first electrode of the plurality of electrodes is operated by the electrical circuitry as a stimulation electrode and includes platinum conductor traces, wherein a second electrode of the plurality of electrodes is operated by the electrical circuitry as a reference electrode and includes a silver or silver-chloride electroplating.

11. The interbody spacer of claim 1, wherein the plurality of load sensors are hermetically encapsulated on the carriers of the interbody spacer.

\* \* \* \* \*